(12) United States Patent
Mizuno et al.

(10) Patent No.: US 12,257,036 B2
(45) Date of Patent: Mar. 25, 2025

(54) BLOOD PRESSURE MEASUREMENT DEVICE

(71) Applicants: OMRON CORPORATION, Kyoto (JP); OMRON HEALTHCARE CO., LTD., Muko (JP)

(72) Inventors: Shinji Mizuno, Yasu (JP); Tomoyuki Nishida, Kyoto (JP); Takashi Ono, Kyoto (JP); Takanori Nishioka, Kyoto (JP); Yoshihiko Sano, Kyoto (JP)

(73) Assignees: OMRON CORPORATION, Kyoto (JP); OMRON HEALTHCARE CO., LTD., Muko (JP)

( * ) Notice: Subject to any disclaimer, the term of this patent is extended or adjusted under 35 U.S.C. 154(b) by 1163 days.

(21) Appl. No.: 16/930,038

(22) Filed: Jul. 15, 2020

(65) Prior Publication Data

US 2020/0345250 A1 Nov. 5, 2020

Related U.S. Application Data

(63) Continuation of application No. PCT/JP2019/000349, filed on Jan. 9, 2019.

(30) Foreign Application Priority Data

Jan. 15, 2018 (JP) .................. 2018-004223

(51) Int. Cl.
*A61B 5/022* (2006.01)
*A61B 5/00* (2006.01)
*A61B 5/0235* (2006.01)

(52) U.S. Cl.
CPC ........ *A61B 5/02233* (2013.01); *A61B 5/0235* (2013.01); *A61B 5/681* (2013.01); *A61B 2562/0219* (2013.01); *A61B 2562/168* (2013.01)

(58) Field of Classification Search
CPC ........... A61B 5/02; A61B 5/021; A61B 5/022; A61B 5/02208–02225; A61B 5/02241;
(Continued)

(56) References Cited

U.S. PATENT DOCUMENTS

2018/0200140 A1* 7/2018 Ganske .................. B32B 27/40
2020/0085319 A1* 3/2020 Lin .......................... F04B 53/10

FOREIGN PATENT DOCUMENTS

CN 106015922 A 10/2016
CN 110267588 A * 9/2019 ......... A61B 5/02233
(Continued)

OTHER PUBLICATIONS

CN_110267588_A_I English translation (Year: 2019).*
(Continued)

*Primary Examiner* — Eric J Messersmith
*Assistant Examiner* — Raymond P Dulman
(74) *Attorney, Agent, or Firm* — Oliff PLC

(57) ABSTRACT

A blood pressure measurement device includes: a base; a flow path cover that is fixed to the base and defines a flow path portion with reference to the base; a recess including an outer surface which is on a base side of the flow path portion and part of which is projected toward the base, and an outer surface which is on a side opposite to the base side and part of which is depressed toward the base; a nozzle that is that is formed on a bottom surface of the recess and communicates with the flow path portion; and a bag-shaped cuff that is connected to the nozzle and that is inflated when a fluid is supplied to an internal space.

3 Claims, 19 Drawing Sheets

(58) Field of Classification Search
CPC ... A61B 5/0235; A61B 5/681; A61B 5/02141; A61B 5/6824; A61B 5/6831; A61B 2562/164; A61B 2562/168; A61B 2562/224; A61B 2562/0247
See application file for complete search history.

(56) References Cited

FOREIGN PATENT DOCUMENTS

| | | | | |
|---|---|---|---|---|
| DE | 102015119996 A1 | * | 5/2017 | |
| JP | 2006-102649 A | | 4/2006 | |
| JP | 2009-089743 A | | 4/2009 | |
| JP | 2010-088513 A | | 4/2010 | |
| JP | 2013-220187 A | | 10/2013 | |
| JP | 2014-033829 A | | 2/2014 | |
| JP | 2017121480 A | * | 7/2017 | ............... A61B 5/02 |
| JP | 2018-000692 A | | 1/2018 | |
| WO | WO-2018133315 A1 | * | 7/2018 | ........... A61B 5/0225 |

OTHER PUBLICATIONS

DE_102015119996_A1_I English translation (Year: 2017).*
Mar. 26, 2019 International Search Report issued in International Patent Application No. PCT/JP2019/000349.
Oct. 25, 2022 Office Action Issued in Chinese Patent Application No. 201980007643.X.

* cited by examiner

F.I.G. 8

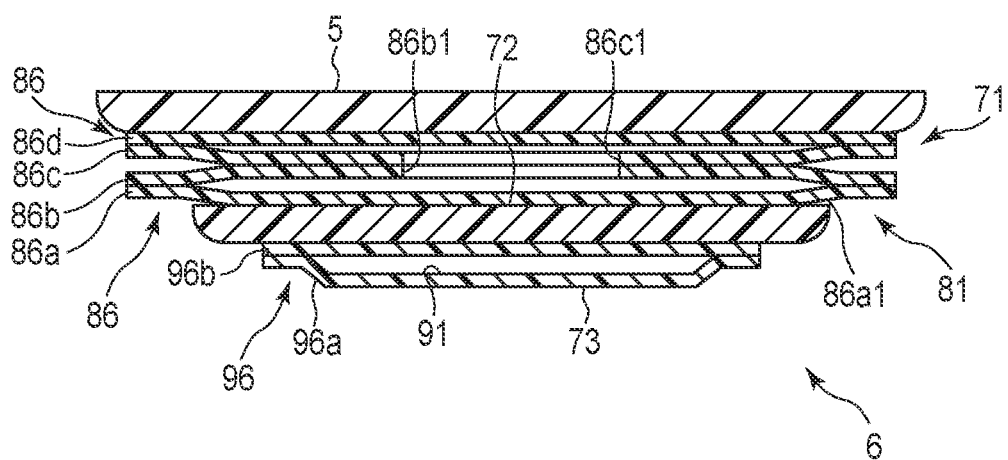
F I G. 13

BLOOD PRESSURE MEASUREMENT DEVICE

CROSS-REFERENCE TO RELATED APPLICATIONS

This is a Continuation Application of PCT application No. PCT/JP2019/000349, filed Jan. 9, 2019, which was published under PCT Article 21(2) in Japanese.

This application is based upon and claims the benefit of priority from Japanese Patent Application No. 2018-004223, filed Jan. 15, 2018, the entire contents of which are incorporated herein by reference.

BACKGROUND

Field

The present invention relates to a blood pressure measurement device that measures blood pressure.

Description of the Related Art

In recent years, blood pressure measurement devices used for measuring blood pressure are used not only in medical facilities but also at home as a means for confirming a health condition. A blood pressure measurement device measures blood pressure by detecting the vibration of the arterial wall, for example, by wrapping a cuff around the upper arm or wrist of a living body, inflating and contracting the cuff, and detecting the pressure of the cuff with a pressure sensor.

As a technique for fluidly connecting the pump in the case of the blood pressure measurement device to the cuff, a nozzle formed on the back surface of the case is used. The nozzle is fluidly connected to the pump within the case. When the cuff is connected to the nozzle, it is fluidly connected to the pump (see, for example, Jpn. Pat. Appln. KOKAI Publication No. 2013-220187).

SUMMARY

It is required that a blood pressure measurement device used at home be thin. However, if the pump and the cuff are fluidly connected to each other by using the nozzle formed on the back surface of the case, the device body and the cuff are aligned in the thickness direction, and the thinning is restricted.

According to one aspect of the invention, a blood pressure measurement device can be provided, which includes a base; a flow path cover that is fixed to the base and defines a flow path portion with reference to the base; a recess including an outer surface which is on a base side of the flow path portion and part of which is projected toward the base, and an outer surface which is on a side opposite to the base side and part of which is depressed toward the base; a nozzle that is that is formed on a bottom surface of the recess and communicates with the flow path portion; and a bag-shaped cuff that is connected to the nozzle and that is inflated when a fluid is supplied to an internal space.

It should be noted here that the flow path portion is a portion of a flow path through which the fluid is made to flow to the cuff. The fluid flowing through the flow path portion includes liquid and air. The cuff is wrapped around the upper arm or wrist of a living body when blood pressure is measured, and is inflated by supplying a fluid thereinto. For example, the cuff is intended to include a pressing cuff of a blood pressure measurement device that measures blood pressure on the wrist, a sensing cuff, and a cuff of a blood pressure measurement device that measures blood pressure on the upper arm. Further, the cuff may be a bag-shaped structure such as an air bag constituting a pressing cuff.

According to this aspect, part of the connecting portion of the cuff connected to the nozzle is arranged inside the recess. Therefore, the thickness of the integrated body made up of the base, the flow path cover and the connecting portion of the cuff can be decreased, so that the blood pressure measurement device can be made thin.

In the aforementioned aspect of the invention, a blood pressure measurement device can be offered, which further includes a projection formed on an end surface of the recess on the base side and located at a position away from a hole of the nozzle.

According to this aspect, when the flow path cover is fixed to the base, the projection comes into contact with the base, so that a gap can be defined between the opening of the nozzle and the base.

In the aforementioned aspect of the invention, a blood pressure measurement device can be offered, which further includes a groove formed in the end surface of the recess on the base side and extending from the hole of the nozzle to an outer peripheral surface of the recess.

According to this aspect, the space between the flow path cover and the base is made continuous with the nozzle by the groove, so that the fluid from the space between the flow path cover and the base can be smoothly guided to the nozzle. Further, the fluid from the nozzle can be smoothly guided to the space between the flow path cover and the base.

According to the present invention, it is possible to provide a blood pressure measurement device that can be made thin.

BRIEF DESCRIPTION OF THE DRAWINGS

FIG. 13 is a cross-sectional view showing a configuration of the curler and cuff structure body.

DETAILED DESCRIPTION

Hereinafter, an example of the blood pressure measurement device 1 according to one embodiment of the present invention will be described with reference to FIGS. 1 to 15.

Figure 1:
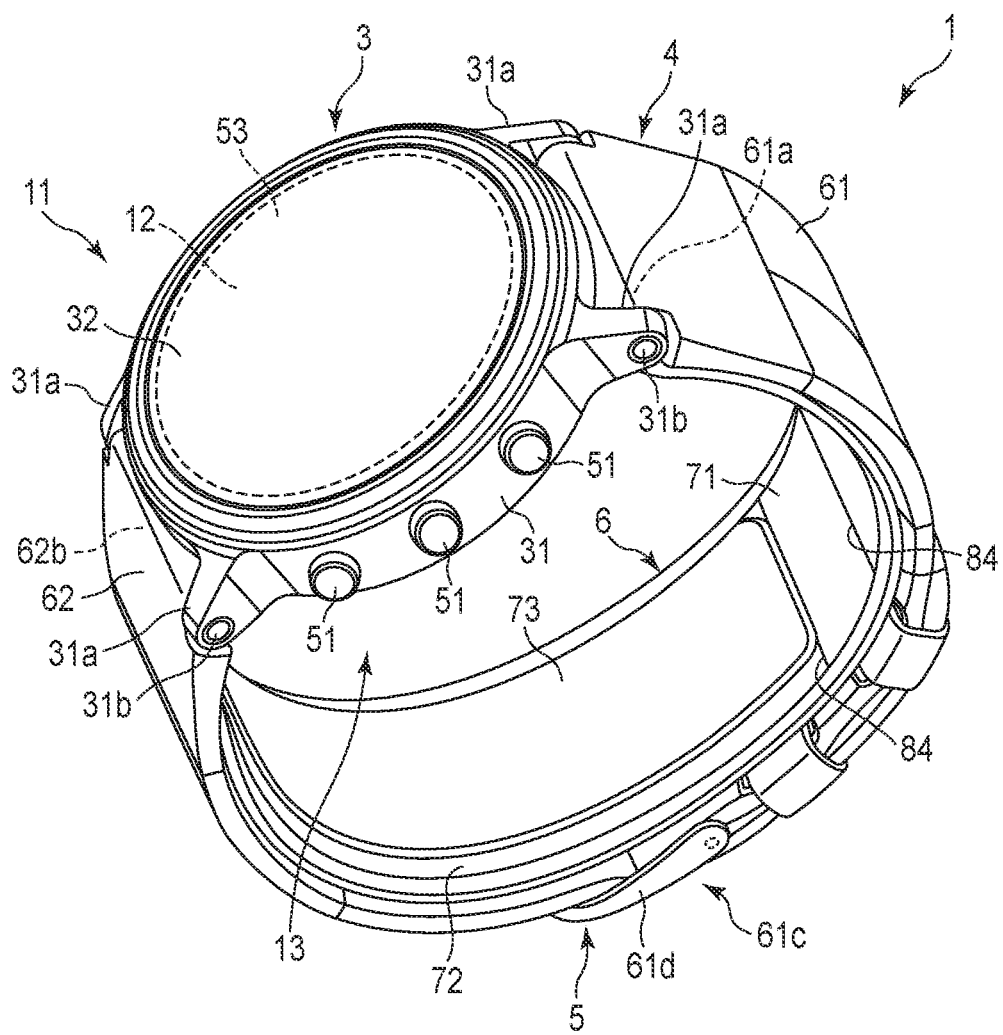
FIG. 1 is a perspective view showing a configuration of a blood pressure measurement device according to an embodiment of the present invention.
Figure 2:
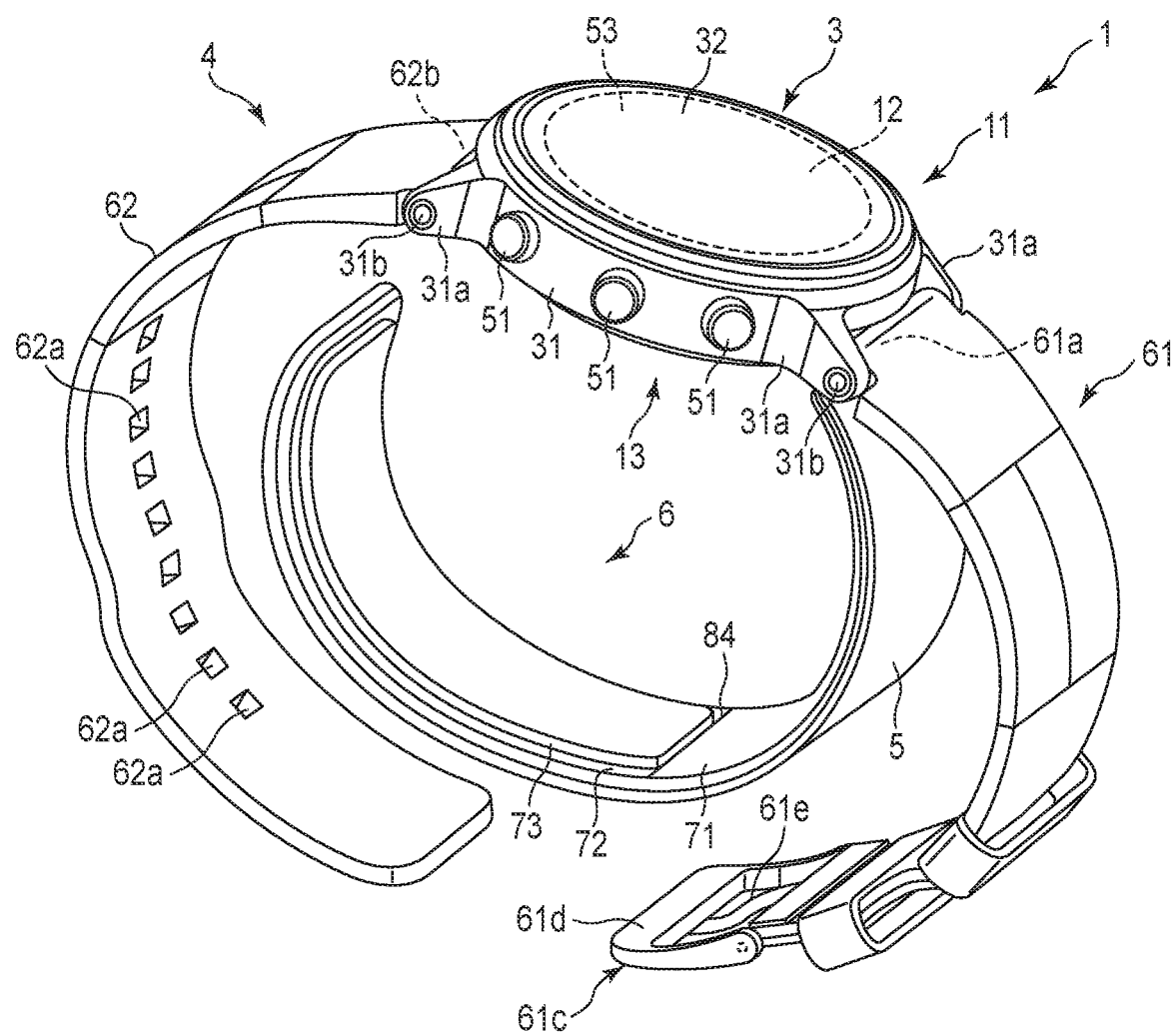
FIG. 2 is a perspective view showing a configuration of the blood pressure measurement device.
Figure 3:
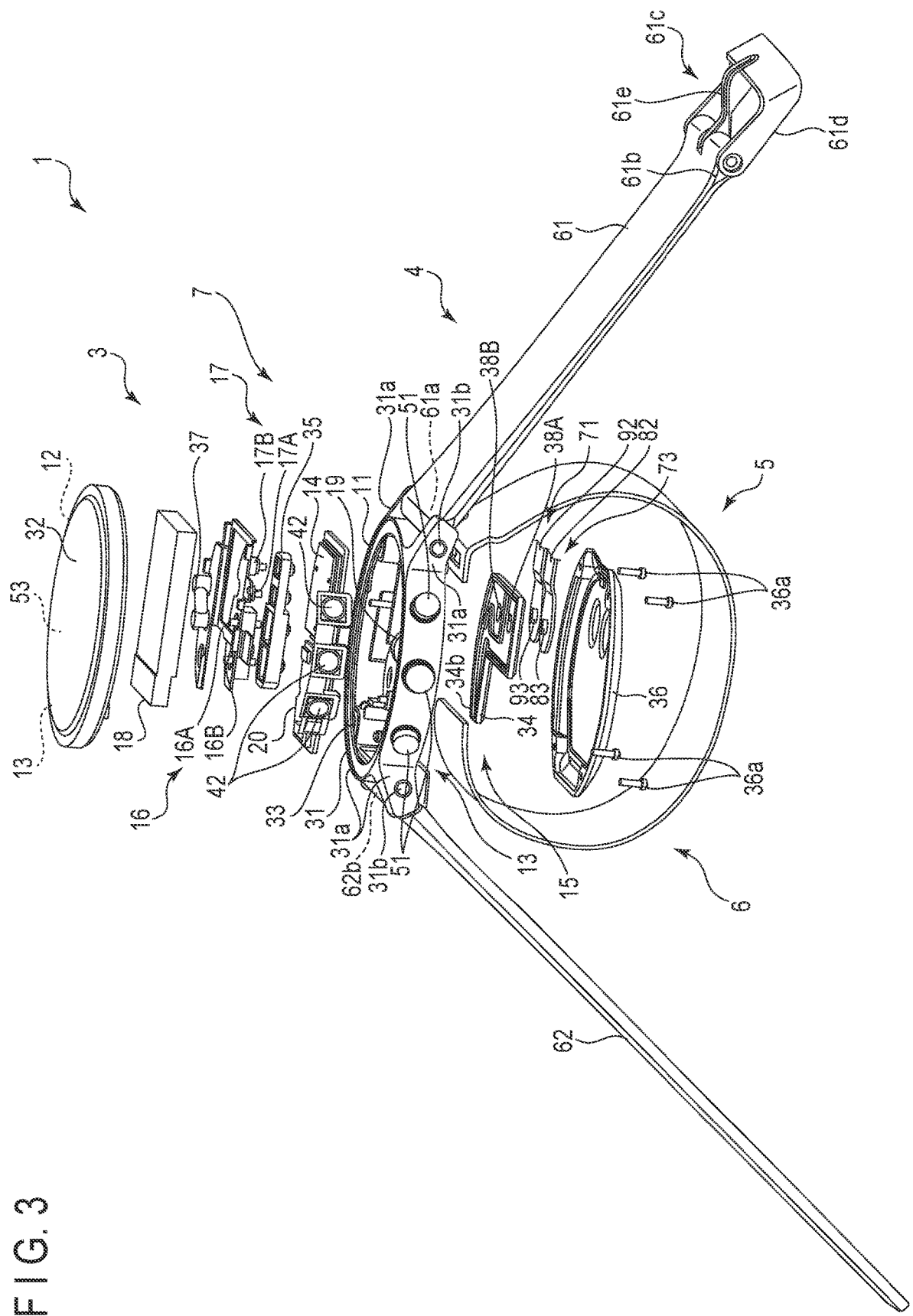
FIG. 3 is an exploded view showing a configuration of the blood pressure measurement device.
Figure 4:
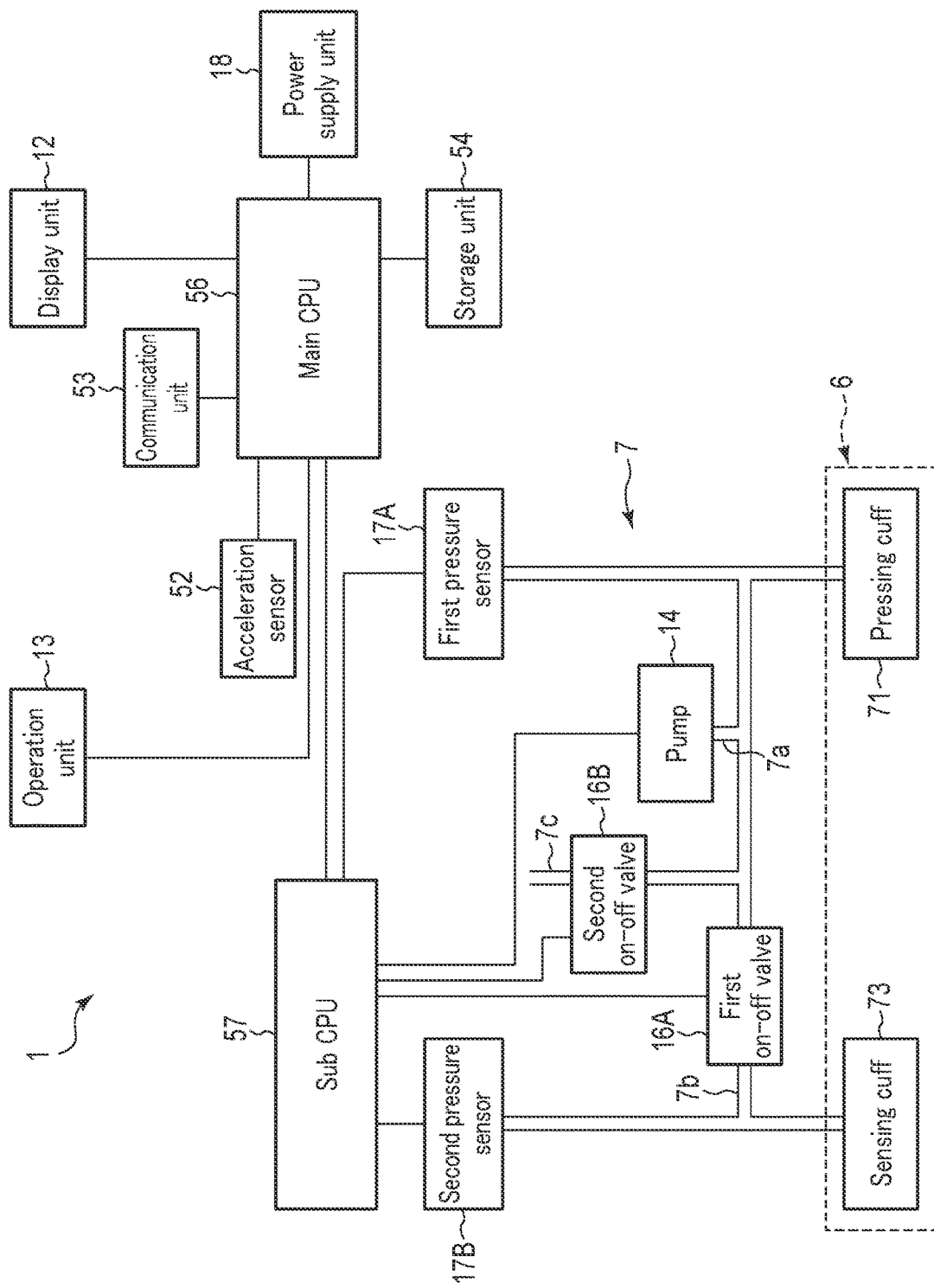
FIG. 4 is a block diagram showing a configuration of the blood pressure measurement device.
Figure 5:
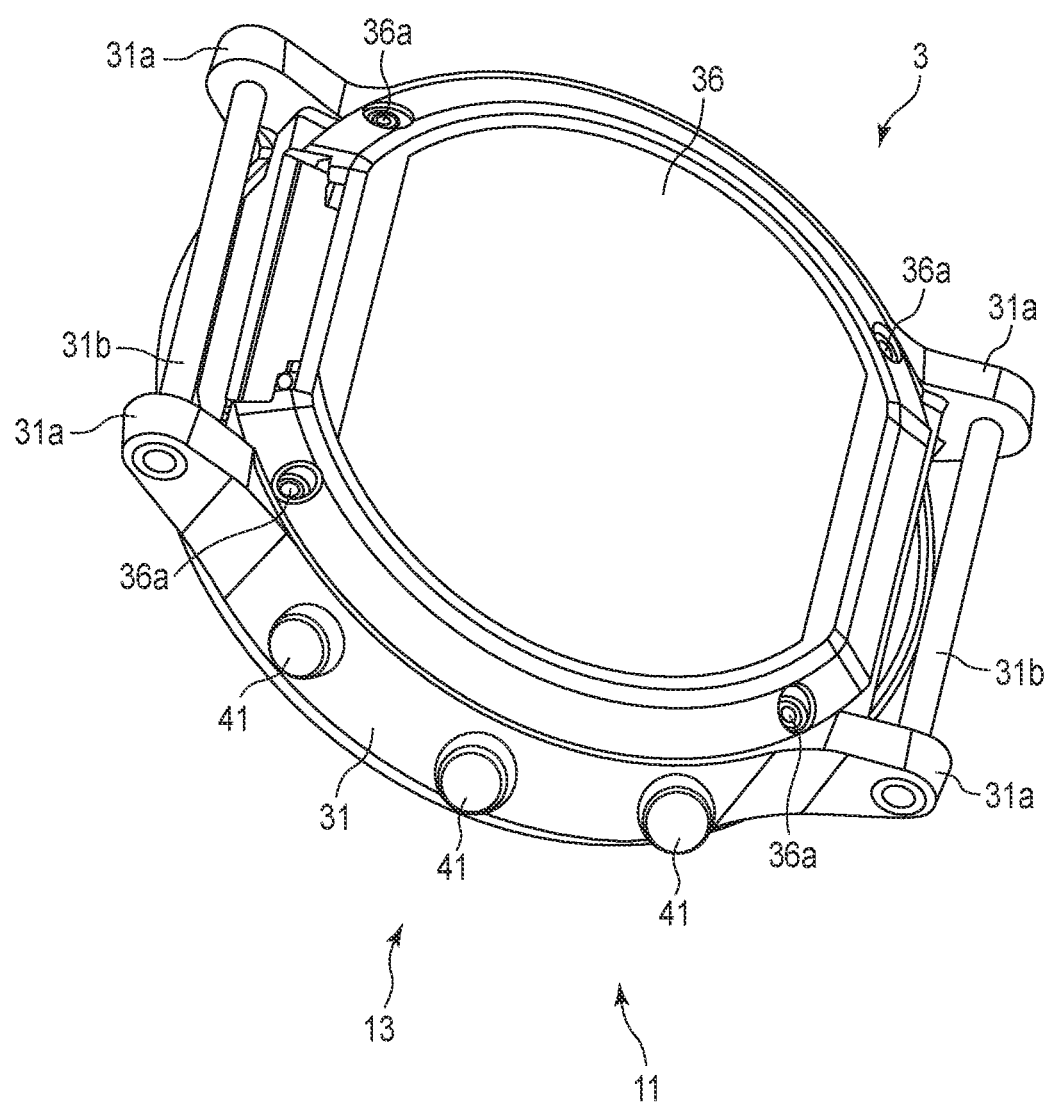
FIG. 5 is a perspective view showing a configuration of a device body of the blood pressure measurement device.
Figure 6:
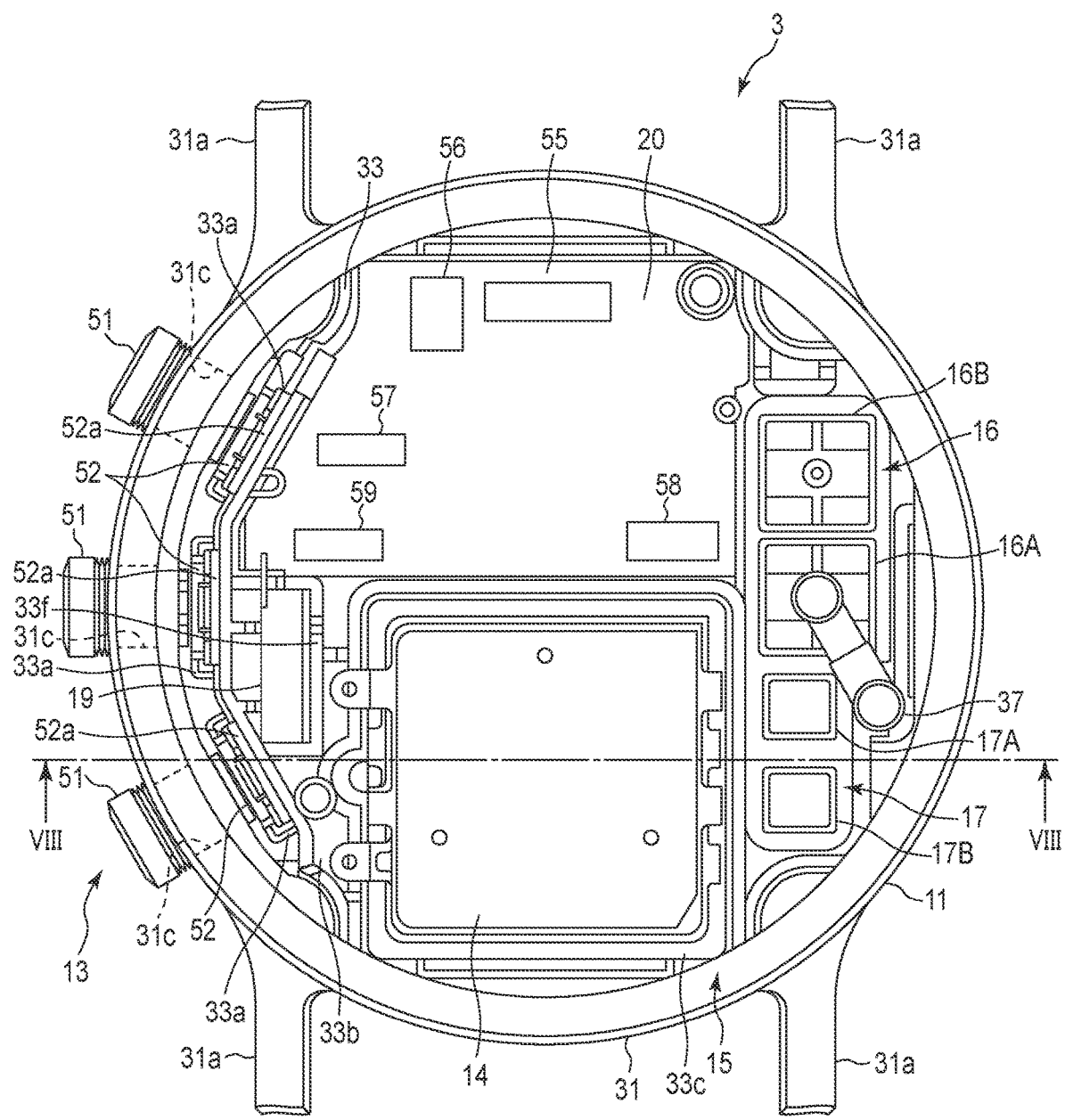
FIG. 6 is a plan view showing an internal configuration of the device body.
Figure 7:
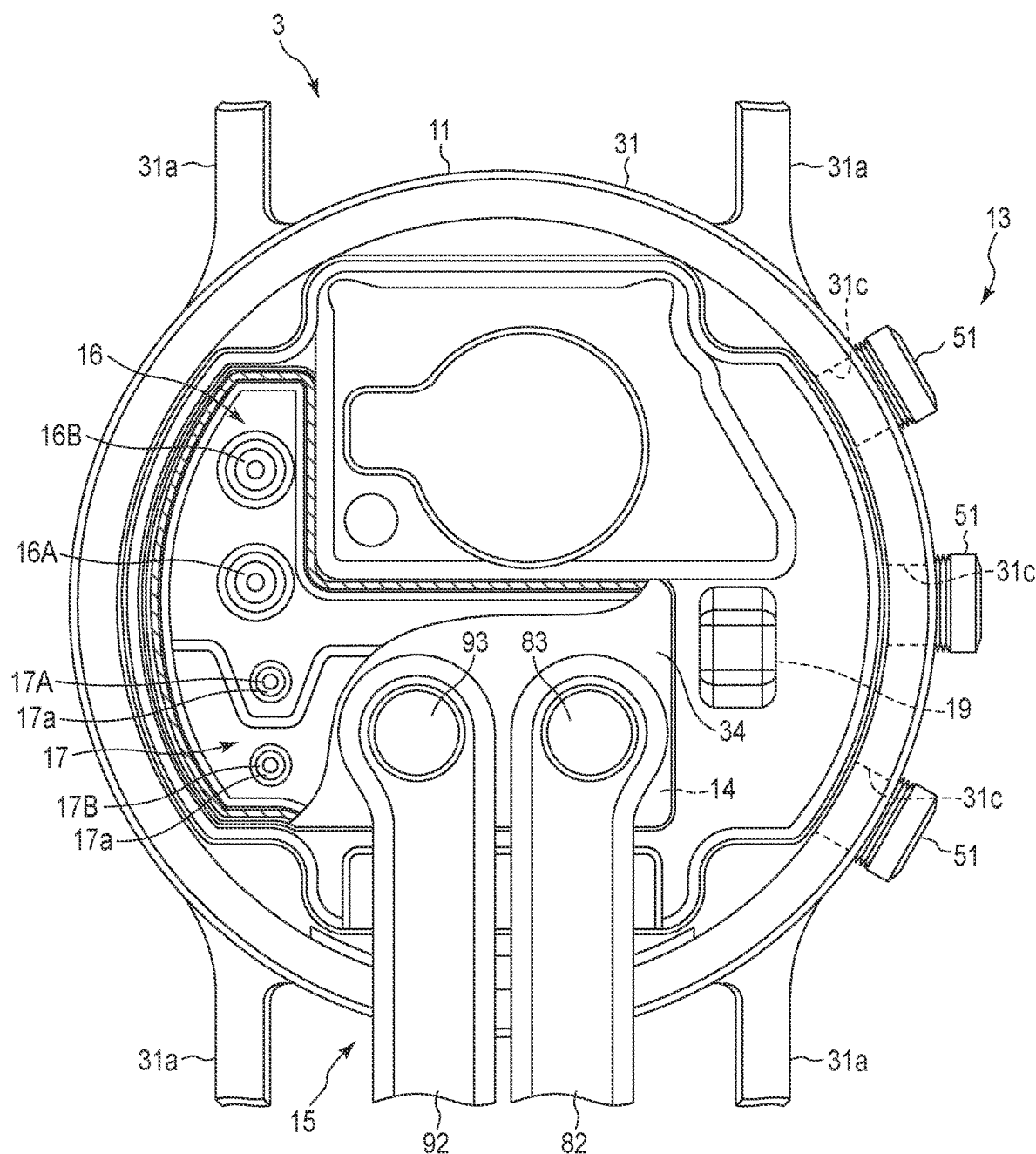
FIG. 7 is a plan view showing an internal configuration of the device body.

FIG. 1 is a perspective view showing how the blood pressure measurement device 1 according to one embodiment of the present invention looks like in a state where a strap 4 is closed. FIG. 2 is a perspective view showing how the blood pressure measurement device 1 looks like in a state where the strap 4 is open. FIG. 3 is an exploded view showing a configuration of the blood pressure measurement device 1. FIG. 4 is a block diagram showing the configuration of the blood pressure measurement device 1. FIG. 5 is a perspective view showing how the device body 3 of the blood pressure measurement device 1 looks like when viewed from the back cover 36 side. FIGS. 6 and 7 are plan views respectively showing how the internal structure of the device body 3 looks like when viewed from the windshield 32 side and the back cover 36 side.

Figure 8:
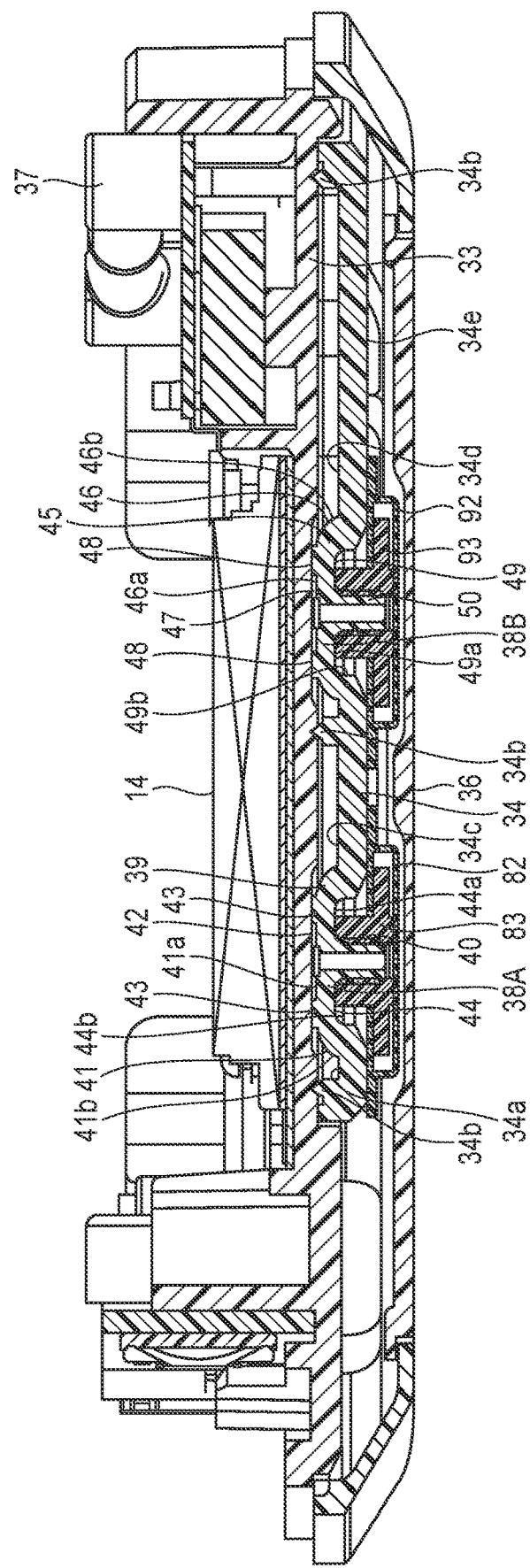
FIG. 8 is a cross-sectional view showing a configuration of the device body of the blood pressure measurement device.
Figure 9:
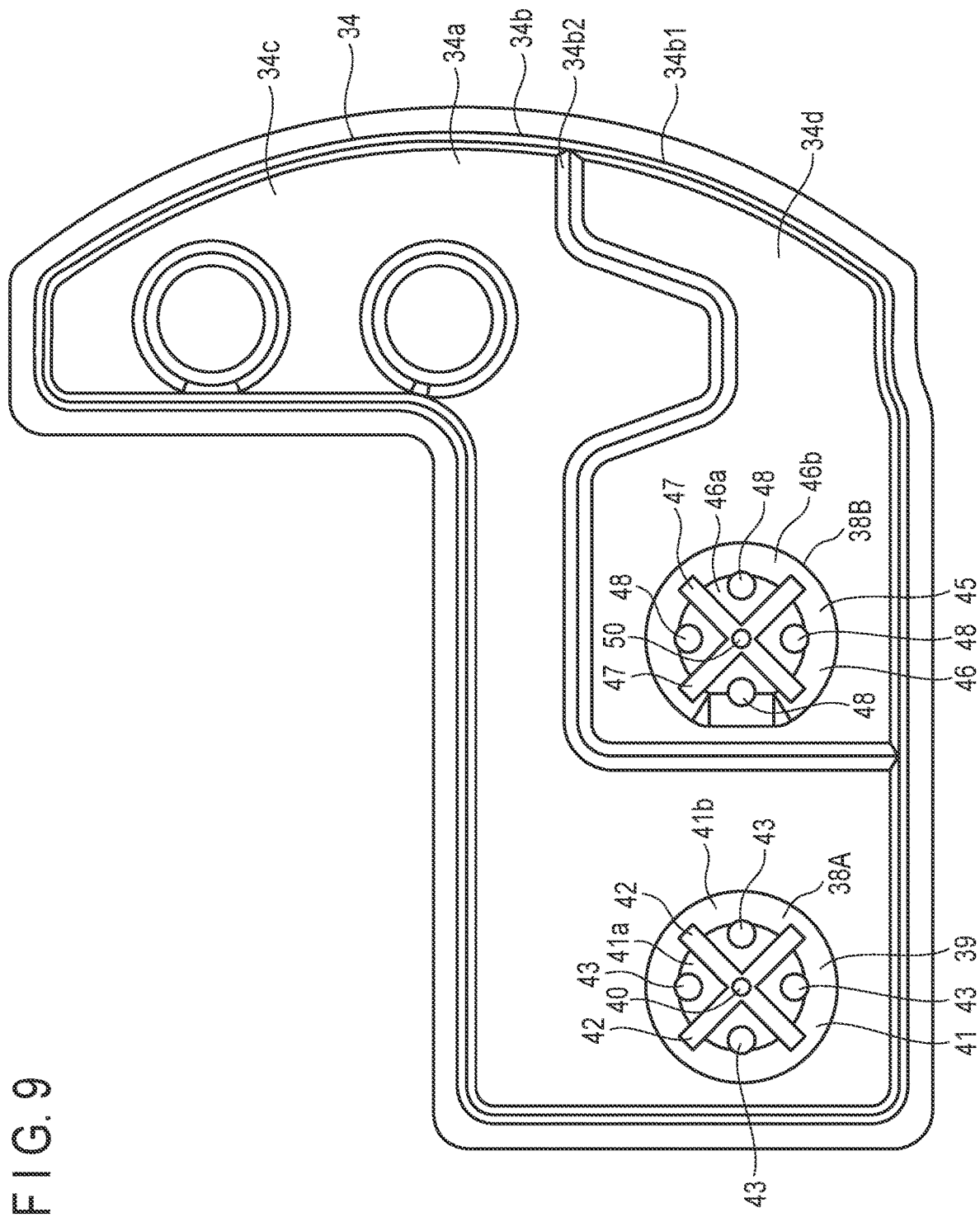
FIG. 9 is a plan view showing a flow path cover used in the blood pressure measurement device.
Figure 10:
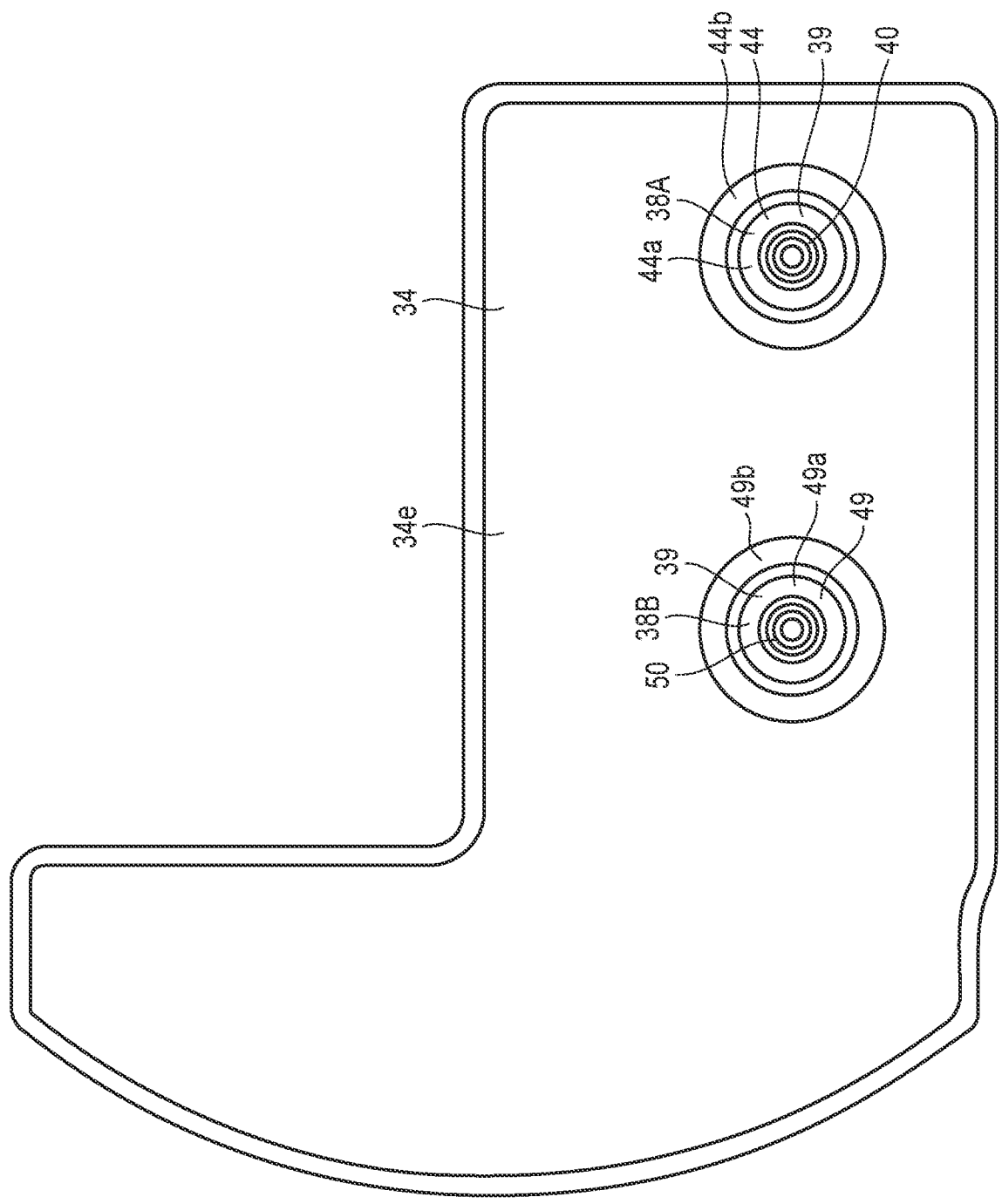
FIG. 10 is a plan view showing the flow path cover.
Figure 11:
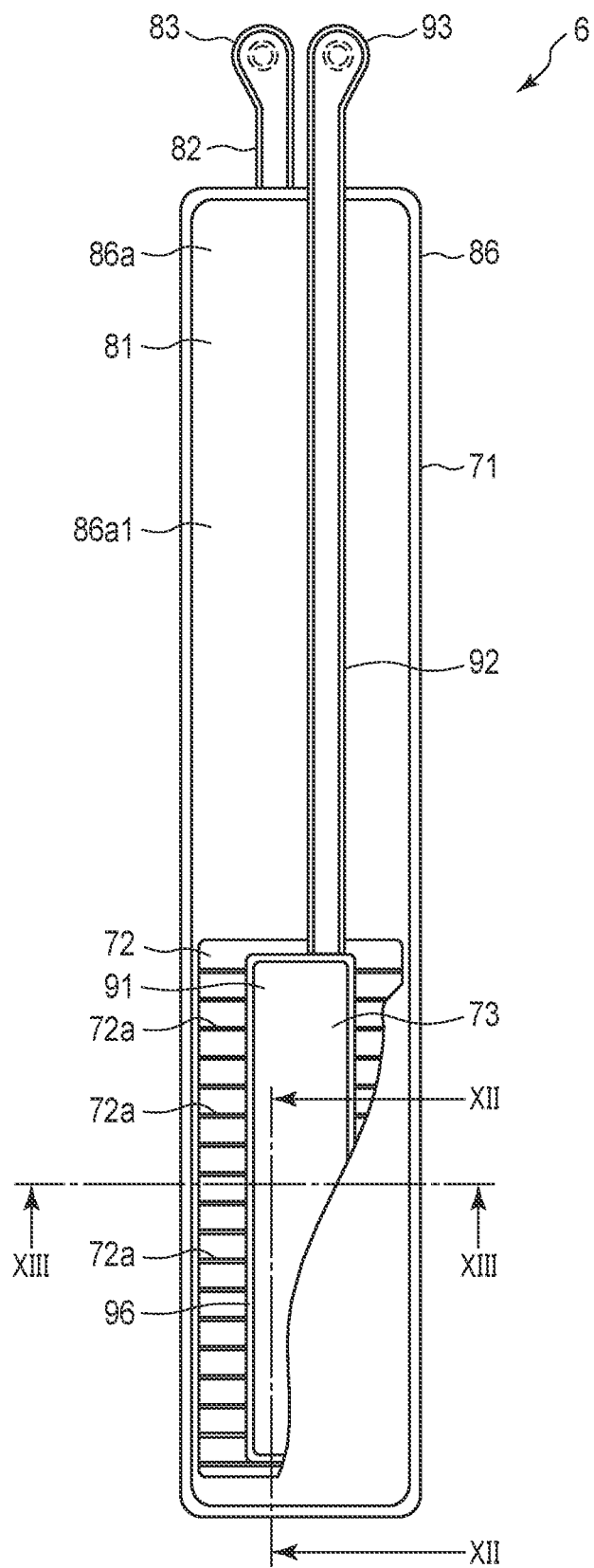
FIG. 11 is a plan view showing a configuration of a cuff structure of the blood pressure measurement device.

FIG. 8 is a cross-sectional view schematically showing the configuration of the device body 3 of the blood pressure measurement device 1 in a section taken along line XIII-XIII in FIG. 6. FIG. 9 is a plan view showing how the flow path cover 34 of the blood pressure measurement device 1 looks like when viewed from the base 33 side. FIG. 10 is a plan view showing how the flow path cover 34 looks like when viewed from the back cover 36 side. FIG. 11 is a plan view showing how the configuration of the cuff structure 6 of the blood pressure measurement device 1 is when viewed from the sensing cuff 73 side.

Figure 12:
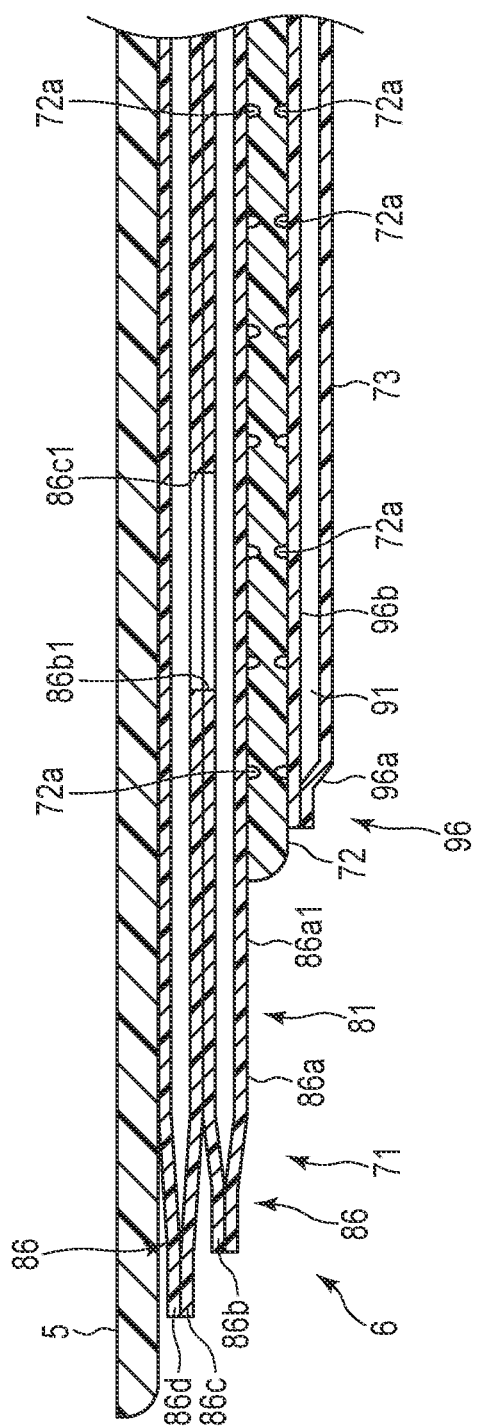
FIG. 12 is a cross-sectional view showing a configuration of a curler and a cuff structure both employed in the blood pressure measurement device.
Figure 14:
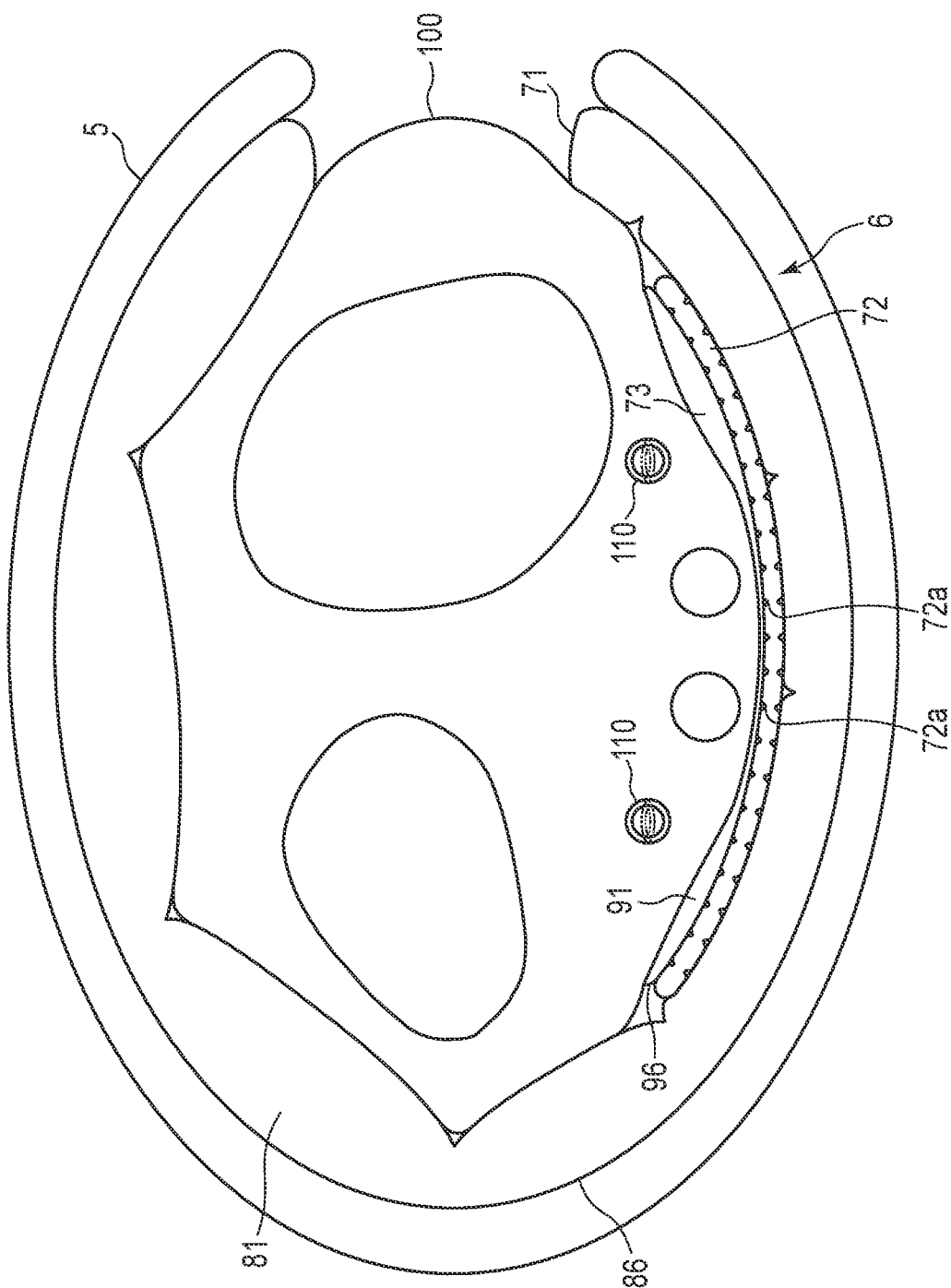
FIG. 14 is a side view schematically showing how a pressing cuff of the cuff structure is when it is inflated.
Figure 15:
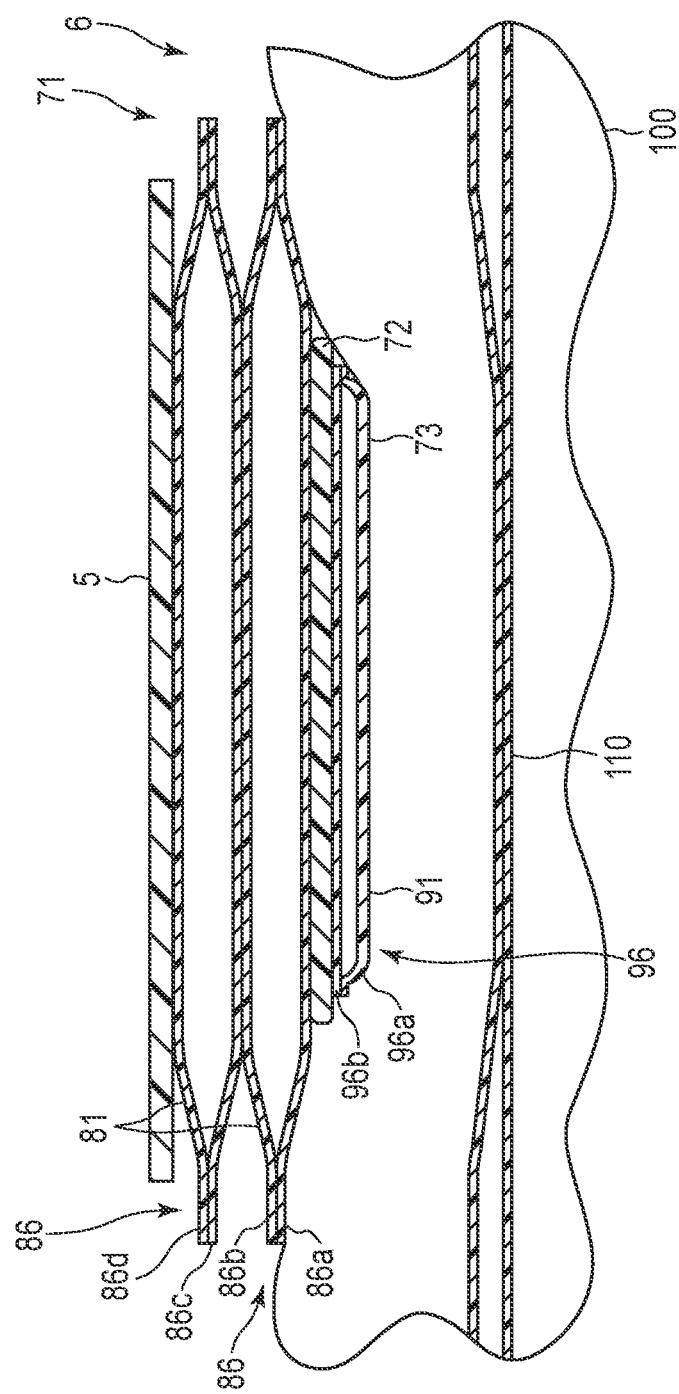
FIG. 15 is a cross-sectional view schematically showing how the pressing cuff of the cuff structure is when it is inflated.

FIG. 12 is a cross-sectional view schematically showing the configuration of the curler 5 and cuff structure 6 of the blood pressure measurement device 1 in a section taken along line XII-XII in FIG. 11. FIG. 13 is a cross-sectional view showing the configuration of the curler 5 and cuff structure 6 in a section taken along line XIII-XIII in FIG. 11. FIGS. 14 and 15 are a side view and a cross section diagram schematically showing an example in which the pressing cuff 71 and sensing cuff 73 of the cuff structure 6 are inflated. In FIG. 12, the curler 5 and the cuff structure 6 are schematically shown as being linear for convenience of illustration, but actually they are curved in the configuration of the blood pressure measurement device 1.

The blood pressure measurement device 1 is an electronic blood pressure measurement device worn on a living body. The present embodiment will be described, referring to an electronic blood pressure measurement device embodied as a wearable device worn on the wrist 100 of the living body. As shown in FIGS. 1 to 15, the blood pressure measurement device 1 comprises a device body 3, a strap 4, a curler 5, a cuff structure 6 including both a pressing cuff 71 and a sensing cuff 73, and a fluid circuit 7.

As shown in FIGS. 1 to 8, the device body 3 comprises a case 11, a display unit 12, an operation unit 13, a pump 14, a flow path portion 15, an on-off valve 16, a pressure sensor 17, a power supply unit 18, a vibration motor 19, and a control board 20. The device body 3 is a supply device that supplies a fluid to the pressing cuff 71 by means of the pump 14, the on-off valve 16, the pressure sensor 17, the control board 20, etc.

The case 11 comprises an outer case 31, a windshield 32 that covers an upper opening of the outer case 31, a base 33 that is provided in the lower region of the inside of the outer case 31, a flow path cover 34 that covers part of the back surface of the base 33, and a back cover 36 that covers the lower portion of the outer case 31. Also, the case 11 comprises a flow path tube 37 that constitutes part of the fluid circuit 7.

The outer case 31 is formed to have a cylindrical shape. The outer case 31 includes two pairs of lugs 31a provided at positions symmetrical in the circumferential direction of the outer peripheral surface, and spring rods 31b respectively provided between the two pairs of lugs 31a. The windshield 32 is a circular glass plate.

The base 33 holds the display unit 12, the operation unit 13, the pump 14, the on-off valve 16, the pressure sensor 17, the power supply unit 18, the vibration motor 19 and the control board 20. In addition, the base 33 constitutes part of the flow path portion 15.

The flow path cover 34 is fixed to the back surface which is the outer surface of the base 33 on the back cover 36 side. The base 33 and the flow path cover 34 form part of the flow path portion 15 by providing a groove in one or both of them.

As shown in the specific example depicted in FIG. 8 and FIG. 9, the flow path cover 34 includes a rib 34b formed on surface 34a, which is an outer surface on the base 33 side when the flow path cover 34 is fixed to the base 33. The rib 34b includes an annular first rib 34b1 formed on the peripheral edge of surface 34a, and a second rib 34b2 that divides a region surrounded by the first rib 34b1 into a first region 34c and a second region 34d.

The region surrounded by the rib 34b serves as a groove. This groove forms part of a flow path portion 15 between the surface 34a and the base 33. The rib 34b is fixed to the back surface of the base 33, for example, by ultrasonic welding.

A first connected portion 38A to which the connecting portion 83 of the tube 82 of the pressing cuff 71 is connected is formed in the first region 34c. A second connected portion 38B to which the connecting portion 93 of the tube 92 of the sensing cuff 73 is connected is formed in the second region 34d.

As shown in FIGS. 8 to 10, the first connected portion 38A includes a recess 39 formed in the flow path cover 34 and a nozzle 40 formed in the recess 39.

The recess 39 is a recess where part of the front surface 34a of the flow path cover 34 is projected toward the base 33 and part of the back surface 34e, i.e., the outer surface on the back cover 36 side, is depressed toward the base 33. The recess 39 is formed by projecting the flow path cover 34 toward the base 33 while keeping the thickness substantially constant.

The surface 41, which is the outer surface of the recess 39 on the base 33 side, includes an end surface 41a, and a peripheral surface 41b that is a portion extending from the portion other than the recess 39 of the surface 34a to the end surface 41a.

A plurality of projections 43 are formed on the end surface 41a, and two grooves 42 are formed therein. The portions of the end surface 41a that are other than the projections 43 and the grooves 42 are formed, for example, such that they are flat surfaces and become parallel to the back surface of the base 33 when the flow path cover 34 is fixed to the back surface of the base 33. The peripheral surface 41b is formed as a curved surface.

The two grooves 42 are formed, for example, such that they are linear and orthogonal to each other at the center of the end surface 41a. Both ends of each of the two grooves 42 extend to the peripheral surface 41b.

The plurality of projections 43 are arranged around the center of the end surface 41a such that one projection 43 is in each of the spaces between the grooves 42. The projections 43 are formed, for example, in a cylindrical shape. The projections 43 come into contact with the back surface of the base 33, so that a gap is maintained between the base 33 and those portions of the end surface 41a which are other than the projections 43.

The back surface 44, which is the outer surface of the recess 39 on the back cover 36 side, includes a bottom surface 44a and an inner peripheral surface 44b that is a portion extending from the portion other than the recess 39 of the surface 34a to the bottom surface 44a. The bottom surface 44a is formed, for example, as a flat surface. The inner peripheral surface 44b is formed, for example, as a cylindrical surface. The edge of the inner peripheral surface 44b is chamfered to have a flat surface, for example.

The nozzle 40 is arranged at the center of the bottom surface 44a. The nozzle 40 is formed to have a cylindrical shape, for example. The nozzle 40 is open at the center of the end surface 41a. The nozzle 40 has, for example, such a length as permits the nozzle 40 to be projected toward the back cover 36 from a portion other than the recess 39 of the back surface 34e of the flow path cover 34.

The second connected portion 38B includes a recess 45 formed in the flow path cover 34 and a nozzle 50 formed in the recess 45.

The recess 45 is a recess where part of the front surface 34a of the flow path cover 34 is projected toward the base 33 and part of the back surface 34e, i.e., the outer surface on the back cover 36 side, is depressed toward the base 33. The recess 45 is formed by projecting the flow path cover 34 toward the base 33 while keeping the thickness substantially constant.

The surface 46, which is the outer surface of the recess 45 on the base 33 side, includes an end surface 46a and a peripheral surface 46b that is a portion extending from the portion other than the recess 45 of the surface 34a to the end surface 46a.

A plurality of projections 48 are formed on the end surface 46a, and two grooves 47 are formed therein. The portions of the end surface 41a that are other than the grooves 47 and the projections 48 are formed, for example, such that they are flat surfaces and become parallel to the back surface of the base 33 when the flow path cover 34 is fixed to the back surface of the base 33. The peripheral surface 46b is formed as a curved surface.

The two grooves 47 are formed, for example, such that they are linear and orthogonal to each other at the center of the end surface 46a. Both ends of each of the two grooves 47 extend to the end surface 46a.

The plurality of projections 48 are arranged around the center of the end surface 46a such that one projection 48 is in each of the spaces between the grooves 47. The projections 48 are formed, for example, in a cylindrical shape. The projections 48 come into contact with the back surface of the base 33, so that a gap is maintained between the base 33 and those portions of the end surface 46a which are other than the projections 48.

The back surface 49, which is the outer surface of the recess 45 on the back cover 36 side, includes a bottom surface 49a and an inner peripheral surface 49b that is a portion extending from the portion other than the recess 39 of the back surface 34e to the bottom surface 49a. The bottom surface 49a is formed, for example, as a flat surface. The inner peripheral surface 49b is formed, for example, as a cylindrical surface. The edge of the inner peripheral surface 49b is chamfered to have a flat surface, for example.

The nozzle 50 is arranged at the center of the bottom surface 49a. The nozzle 50 is formed to have a cylindrical shape, for example. The nozzle 50 is open at the center of the end surface 46a. The nozzle 40 has, for example, such a length as permits the nozzle 40 to be projected toward the back cover 36 from a portion other than the recess 45 of the back surface 34e of the flow path cover 34.

The back cover 36 covers the living body side end of the outer case 31. The back cover 36 is fixed to the outer case 31 or to the living body side end of the base 33 with, for example, four screws 36a.

The flow path tube 37 constitutes part of the flow path portion 15. The flow path tube 37 connects, for example, the on-off valve 16 and part of the flow path portion 15 of the base 33.

The display unit 12 is arranged on the base 33 of the outer case 31 and directly below the windshield 32. The display unit 12 is electrically connected to the control board 20. The display unit 12 is, for example, a liquid crystal display or an organic electroluminescence display. The display unit 12 displays various information, including a date and time, blood pressure values such as systolic blood pressure and diastolic blood pressure, and measurement results such as a heart rate.

The operation unit 13 is configured to enable commands to be entered from a user. For example, the operation unit 13 includes a plurality of buttons 51 provided on the case 11, a sensor 52 that detects an operation of the buttons 51, and a touch panel 53 provided on either the display unit 12 or the windshield 32. The operation unit 13 is operated by a user and converts a command into an electric signal. The sensor 52 and the touch panel 53 are electrically connected to the control board 20 and output an electric signal to the control board 20.

For example, three buttons 51 are provided. The buttons 51 are supported on the base 33 and are projected from the outer peripheral surface of the outer case 31. The plurality of buttons 51 and a plurality of sensors 52 are supported on the base 33. The touch panel 53 is provided, for example, integrally with the windshield 32.

The pump 14 is, for example, a piezoelectric pump. The pump 14 compresses air and supplies the compressed air to the cuff structure 6 via the flow path portion 15. The pump 14 is electrically connected to the control unit 59.

The flow path portion 15 is an air flow path configured by a groove or the like provided in the flow path cover 34 that covers the major surface on the back cover 36 side of the base 33 and on the back cover 36 side of the base 33. The flow path portion 15 constitutes a flow path that connects the pump 14 to the pressing cuff 71 and a flow path that connects the pump 14 to the sensing cuff 73. In addition, the flow path portion 15 constitutes a flow path that connects the pressing cuff 71 to the atmosphere and a flow path that connects the sensing cuff 73 to the atmosphere.

The on-off valve 16 opens or closes part of the flow path portion 15. For example, a plurality of on-off valves 16 are provided, and a combination of the open/closed states of the on-off valves 16 selectively opens or closes a flow path connecting the pump 14 to the pressing cuff 71, a flow path connecting the pump 14 to the sensing cuff 73, and a flow path connecting the pressing cuff 71 to the atmosphere and a flow path connecting the sensing cuff 73 to the atmosphere. For example, two on-off valves 16 are used.

The pressure sensor 17 detects pressure of the pressing cuff 71 and the sensing cuff 73. The pressure sensor 17 is electrically connected to the control board 20. The pressure sensor 17 is electrically connected to the control board 20, converts detected pressure into an electric signal, and outputs the electric signal to the control board 20. The pressure sensor 17 is provided, for example, in a flow path connecting the pump 14 to the pressing cuff 71 and a flow path connecting the pump 14 to the sensing cuff 73. Since these flow paths are continuous with the pressing cuff 71 and the sensing cuff 73, the pressure in these flow paths is equal to the pressures in the internal spaces of the pressing cuff 71 and sensing cuff 73.

The power supply unit 18 is, for example, a secondary battery such as a lithium ion battery. The power supply unit 18 is electrically connected to the control board 20. The power supply unit 18 supplies power to the control board 20.

The vibration motor 19 is arranged in the motor support portion 33f as shown in FIG. 6. In a specific example, the vibration motor 19 is forcibly inserted and fitted into the motor support portion 33f. The vibration motor 19 is an example of the drive unit of the present invention.

As shown in FIGS. 4 and 6, the control board 20 comprises, for example, a board 55, an acceleration sensor 56, a communication unit 57, a storage unit 58, and a control unit 59. The control board 20 is configured by mounting the acceleration sensor 56, the communication unit 57, the storage unit 58, and the control unit 59 on the board 55.

The board 55 is fixed to the base 33 of the case 11 with screws or the like.

The acceleration sensor 56 is, for example, a triaxial acceleration sensor. The acceleration sensor 56 outputs, to the control unit 59, an acceleration signal representing accelerations that are applied to the device body 3 in three directions orthogonal to each other. For example, the acceleration sensor 56 is used to measure the activity amount of the living body wearing the blood pressure measurement device 1 based on detected accelerations.

The communication unit 57 is configured to transmit/receive information to/from an external device wirelessly or by wire. The communication unit 57 transmits, for example, information controlled by the control unit 59 and information such as a measured blood pressure value and a pulse rate to an external device via a network. Also, the communication unit 57 receives a software update program or the like from the external device via the network and sends it to the control unit.

In the present embodiment, the network is, for example, the Internet, but the network is not limited to this, and may be a network such as a LAN (Local Area Network) in a hospital, or direct communications with an external device that are performed using a cable with a predetermined standard terminal such as USB. Therefore, the communication unit 57 may include a plurality of wireless antennas, micro USB connectors, etc.

The storage unit 58 stores in advance program data for controlling the entire blood pressure measurement device 1 and the fluid circuit 7, setting data for setting various functions of the blood pressure measurement device 1, calculation data for calculating blood pressure values and pulses based on the pressure measured by the pressure sensor 17, etc. Also, the storage unit 58 stores information such as measured blood pressure values and pulses.

The control unit 59 includes a single CPU or a plurality of CPUs, and controls the operation of the entire blood pressure measurement device 1 and the operation of the fluid circuit 7. The control unit 59 is electrically connected to the display unit 12, the operation unit 13, the pump 14, the on-off valves 16 and the pressure sensors 17, and supplies electric power to them. Further, the control unit 59 controls the operations of the display unit 12, pump 14 and the on-off valves 16 based on electric signals output from the operation unit 13 and the pressure sensors 17.

For example, as shown in FIG. 4, the control unit 59 includes a main CPU 56 that controls the operation of the entire blood pressure measurement device 1, and also includes a sub CPU 57 that controls the operation of the fluid circuit 7. For example, when a command for measuring blood pressure is input from the operation unit 13, the sub CPU 57 drives the pump 14 and the on-off valves 16 and supplies compressed air to the pressing cuff 71 and the sensing cuff 73.

Also, the sub CPU 57 controls the driving and stopping of the pump 14 and the opening and closing of the on-off valves 16, based on electric signals output from the pressure sensors 17, to selectively supply compressed air to the pressing cuff 71 and the sensing cuff 73, and also selectively decreases the pressures in the pressing cuff 71 and the sensing cuff 73. The main CPU 56 obtains measurement results such as blood pressure values, e.g., systolic blood pressure and diastolic blood pressure, and a heart rate, based on electric signals output from the pressure sensors 17, and outputs an image signal corresponding to the measurement results to the display unit 12.

As shown in FIGS. 1 to 3, the strap 4 includes a first strap 61 provided for one pair of lugs 31a and the spring rod 31b, and a second strap 62 provided for the other pair of lugs 31a and the spring rod 31b.

The first strap 61 is referred to as a parent and is formed to have a band shape. The first strap 61 is includes a first hole portion 61a provided at one end portion and being orthogonal to the longitudinal direction of the first strap 61, a second hole portion 61b provided at the other end portion and being orthogonal to the longitudinal direction of the first strap 61, and a buckle 61c provided for the second hole portion 61b. The first hole portion 61a can receive the spring rod 31b inserted thereinto and has an inner diameter permitting the first strap 61 to rotate with respect to the spring rod 31b. That is, the first strap 61 is rotatably held by the outer case 31 between the pair of lugs 31a and with the spring rod 31b being within the first hole portion 61a.

The second hole portion 61b is provided at the tip end of the first strap 61.

The buckle 61c includes a rectangular frame-shaped body 61d and a stick 61e rotatably attached to the frame-shaped body 61d. One side of the frame-shaped body 61d, to which the stick 61e is attached, is inserted into the second hole portion 61b and is rotatably attached with respect to the first strap 61.

The second strap 62 is referred to as a sword tip and is formed to have a strap shape with a width that enables insertion into the frame-shaped body 61d. The second strap 62 has a plurality of small holes 62a into which the stick 61e can be inserted.

When the second strap 62 is inserted into the frame-shaped body 61d and the stick 61e is inserted into one small hole 62a, and the first strap 61 and the second strap 62 are integrally connected thereby, the strap 4 mentioned above cooperates with the outer case 31 and forms an annular shape in conformity with the circumferential direction of the wrist 100.

The curler 5 is formed of a resin material and has a band shape that curves along the circumferential direction of the wrist. The curler 5 is configured, for example, such that one end is fixed between the base 33 and flow path cover 34 of the device body 3 and the back cover 36, and the other end is arranged close to the device body 3.

As shown in FIGS. 1 to 3 and FIG. 14, the curler 5 is formed of a resin material having a shape that is curved along the circumferential direction of the wrist 100 in a side view viewed in a direction orthogonal to the circumferential direction of the wrist, i.e., in the longitudinal direction of the wrist. The curler 5 extends from the device body such that it extends from the back of the wrist to the palm by way of one side and further to the central side on the other side. That is, the curler 5 is curved along the circumferential direction of the wrist so as to cover most of the circumferential direction of the wrist 100, and both ends of the curler 5 are separate by a predetermined distance.

The curler 5 has such hardness as provides both flexibility and shape retention. The flexibility mentioned here means that the shape of the curler 5 is deformed in the radial direction when an external force is applied thereto. For example, when the curler 5 is pressed by the strap 4, the curler 5 moves closer to the wrist, or the shape of the curler 5 becomes similar to that of the wrist or moves in conformity with the shape of the wrist in a side view. The shape retention means that the curler 5 can maintain a pre-fabricated shape when an external force is not applied, and in the present embodiment, the shape of the curler 5 can maintain a shape that curves along the circumferential direction of the wrist. The curler 5 is formed of a resin material. The curler 5 is formed of, for example, polypropylene and has a thickness of approximately 1 mm. The curler 5 holds the cuff structure 6 along the inner surface shape of the curler 5.

As shown in FIGS. 1 to 4 and FIGS. 11 to 13, the cuff structure 6 comprises a pressing cuff 71, a back plate 72 and a sensing cuff 73. The cuff structure 6 is a structure formed by integrally stacking the pressing cuff 71, the back plate 72 and the sensing cuff 73. The cuff structure 6 is fixed to the inner surface of the curler 5.

The pressing cuff 71 is an example of a cuff. The pressing cuff 71 is fluidly connected to the pump 14 via the flow path portion 15. The pressing cuff 71 inflates and presses the back plate 72 and the sensing cuff 73 against the living body. The pressing cuff 71 comprises a plurality of air bags 81, a tube 82 that communicates with the air bags 81, and a connecting portion 83 provided at the tip of the tube 82.

The air bag 81 is a bag-shaped structure. Since the blood pressure measurement device 1 of the present embodiment is configured to use air supplied by the pump 14, a description will be given of the air bag. Where a fluid other than air is used, the bag-shaped structure may be a fluid bag such as a liquid bag.

The plurality of air bags 81 are stacked and fluidly communicate with each other in the stacking direction. In a specific example, the pressing cuff 71 includes two-layer air bags 81 that fluidly communicate with each other in the stacking direction, a tube 82 provided at one longitudinal end of one of the air bags 81, and a connecting portion 83 provided at the tip of the tube 82.

The major surface of one of the air bags 81 of the pressing cuff 71 is fixed to the inner surface of the curler 5. For example, the pressing cuff 71 is attached to the inner surface of the curler 5 with a double-sided adhesive tape or with an adhesive agent.

The two-layer air bags 81 have a rectangular shape elongated in one direction. For example, each air bag 81 is formed by combining two sheet members 86 that are elongated in one direction and welding the edges by heat. In a specific example, as shown in FIGS. 11 to 13, the two-layer air bags 81 includes, from the living body side, a first sheet member 86a, a second sheet member 86b forming the first layer air bag 81 together with the first sheet member 86a, a third sheet member 86c integrally adhered to the second sheet member 86b, and a fourth sheet member 86d forming the second layer air bag 81 together with the third sheet member 86c.

The first sheet member 86a and the second sheet member 86b form the air bag 81 by welding the peripheral portions of the four sides. The second sheet member 86b and the third sheet member 86c are arranged to face each other, and respectively include a plurality of openings 86b1 and 86c1 that fluidly connect the two air bags 81. An adhesive layer or a double-sided adhesive tape is provided on the curler 5 side outer surface of the fourth sheet member 86d, and the fourth sheet member 86d is adhered to the curler 5 with the adhesive layer or with the double-sided adhesive tape.

The third sheet member 86c and the fourth sheet member 86d form the air bag 81 by welding the peripheral portions of the four sides. Further, for example, a tube 82 that is fluidly continuous with the internal space of the air bag 81 is arranged on one side of the third sheet member 86c and the fourth sheet member 86d, and is fixed by welding. For example, the third sheet member 86c and the fourth sheet member 86d form the air bag 81 by welding the peripheral portions of the four sides, with the tube 82 being arranged between the third sheet member 86c and the fourth sheet member 86d. By doing so, the tube 82 is integrally welded.

The tube 82 is connected to one of the two-layer air bags 81 and is provided at one longitudinal end of that air bag 81. In a specific example, the tube 82 is provided on the curler 5 side of the two-layer air bags 81 and at the end close to the device body 3. The tube 82 has a connecting portion 83 at the tip. The tube 82 constitutes a flow path between the device body 3 and the air bag 81 in the fluid circuit 7.

As shown in FIG. 8, the connecting portion 83 is a nipple into which the nozzle 40 of the first connected portion 38A of the flow path cover 34 is fitted. The connecting portion 83 is formed to have a cylindrical shape, for example. With the nozzle 40 fitted inside, the connecting portion 83 provides a seal between the outer peripheral surface of the connecting portion 83 and the inner peripheral surface of the nozzle 40. In the axial direction, the connecting portion 83 has, for example, such a length as permits the tip of the connecting portion 83 to come into contact with the bottom surface 44a of the recess 39. In this manner, where the connecting portion 83 has a length capable of coming into contact with the bottom surface 44a, the nozzle 40 may be inserted into the connecting portion 83 until the tip of the connecting portion 83 comes into contact with the bottom surface 44a.

The back plate 72 is adhered to the outer surface 86a1 of the first sheet member 86a of the pressing cuff 71 with an adhesive layer, a double-sided adhesive tape, or the like. The back plate 72 is formed of a resin material and has a plate shape. The back plate 72 is formed of polypropylene, for example, and is formed as a plate shape having a thickness of approximately 1 mm. The back plate 72 has a shape following property.

The shape-following property mentioned here refers to a function in which the back plate 72 can be deformed in conformity with the shape of the contacted portion of the wrist 100, and the contacted portion of the wrist 100 is a portion that is brought into contact with the back plate 72. The contact mentioned here includes both direct contact and indirect contact.

Therefore, the shape-following property means that the back plate 72 provided on the pressing cuff 71, or the back plate 72 provided between the pressing cuff 71 and the sensing cuff 73, is deformable such that the back plate 72 itself or the sensing cuff 73 provided on the back plate 72 is deformable in conformity with the wrist 100 and comes into tight contact with the wrist 100.

For example, the back plate 72 has a plurality of grooves 72a in both major surfaces of the back plate 72 at opposing positions that are at equal intervals in the longitudinal direction of the back plate 72. Since the back plate 72 is thinner at portions where the grooves 72a are provided than at portions where no grooves are provided, the portions where the grooves 72a are provided are easily deformable. Thus, the back plate 72 has a shape-following property that deforms in conformity with the shape of the wrist 100. The back plate 72 has a length that covers the palm side of the wrist 100. The back plate 72 transmits a pressing force from the pressing cuff 71 to the back plate 72 side major surface of the sensing cuff 73 while conforming to the shape of the wrist 100.

The sensing cuff 73 is fixed to the living body side major surface of the back plate 72. As shown in FIG. 14, the sensing cuff 73 is brought into direct contact with that region of the wrist 100 where the artery exists. The sensing cuff 73 is formed to have the same shape as the back plate 72 or to have a shape smaller than the back plate 72, when it is viewed in the longitudinal direction and the width direction of the back plate 72. When the sensing cuff 73 is inflated, the sensing cuff 73 compresses the region where the palm side artery 110 of the wrist 100 exists. The sensing cuff 73 is pressed against the living body by the inflated pressing cuff 71, with the back plate 72 interposed.

In a specific example, the sensing cuff 73 comprises one air bag 91, a tube 92 that communicates with the air bag 91, and a connecting portion 93 provided at the tip of the tube 92. The sensing cuff 73 has one major surface of the air bag 91 fixed to the back plate 72. For example, the sensing cuff 73 is adhered to the living body side major surface of the back plate 72 with a double-sided adhesive tape, an adhesive layer, or the like.

The air bag 91 is a bag-shaped structure. Since the blood pressure measurement device 1 of the present embodiment is configured to use air supplied by the pump 14, a description will be given of the air bag. Where a fluid other than air is used, the bag-shaped structure may be a liquid bag or the like. A plurality of air bags 91 are stacked and fluidly communicate with each other in the stacking direction.

The air bag 91 has a rectangular shape elongated in one direction. For example, each air bag 91 is formed by combining two sheet members that are elongated in one direction and welding the edges by heat. In a specific example, as shown in FIGS. 12 and 13, the air bag 91 includes, from the living body side, a fifth sheet member 96a and a sixth sheet member 96b.

For example, a tube 92 that is fluidly continuous with the internal space of the air bag 91 is arranged on one side of the fifth sheet member 96a and the sixth sheet member 96b, and the fifth sheet member 96a and the sixth sheet member 96b are fixed by welding. For example, the fifth sheet member 96a and the sixth sheet member 96b form the air bag 91 by welding the peripheral portions of the four sides, with the tube 92 being arranged between the fifth sheet member 96a and the sixth sheet member 96b. By doing so, the tube 92 is integrally welded.

The tube 92 is provided at one longitudinal end of the air bag 91. In a specific example, the tube 92 is provided at that end of the air bag 91 which is closer to the device body 3. The tube 92 has a connecting portion 93 at the tip. The tube 92 constitutes a flow path between the device body 3 and the air bag 91 in the fluid circuit 7.

As shown in FIG. 8, the connecting portion 93 is a nipple into which the nozzle 50 of the second connected portion 38B of the flow path cover 34 is fitted. The connecting portion 93 is formed to have a cylindrical shape, for example. With the nozzle 50 fitted inside, the connecting portion 93 provides a seal between the outer peripheral surface of the connecting portion 93 and the inner peripheral surface of the nozzle 40. In the axial direction, the connecting portion 93 has, for example, such a length as permits the tip of the connecting portion 93 to come into contact with the bottom surface 49a of the recess 45. In this manner, where the connecting portion 93 has a length capable of coming into contact with the bottom surface 49a, the nozzle 50 may be inserted into the connecting portion 93 until the tip of the connecting portion 93 comes into contact with the bottom surface 49a.

The sheet members 86 and 96 forming the pressing cuff 71 and the sensing cuff 73 are formed of a thermoplastic elastomer. Examples of the thermoplastic elastomer with which the sheet members 86 and 96 are formed include thermoplastic polyurethane resin (Thermoplastic PolyUrethane, hereinafter referred to as TPU), vinyl chloride resin (Polyvinyl Chloride), ethylene vinyl acetate resin (Ethylene-Vinyl Acetate), thermoplastic polystyrene resin (Thermoplastic PolyStyrene), thermoplastic polyolefin resin (Thermoplastic PolyOlefin), thermoplastic polyester resin (ThermoPlastic Polyester), and thermoplastic polyamide resin (Thermoplastic PolyAmide). TPU is preferably used as the thermoplastic elastomer. The sheet members may have a single-layer structure or a multi-layer structure.

The sheet members 86 and 96 are not limited to the thermoplastic elastomer, and may be a thermosetting elastomer such as silicone. Further, a combination of a thermoplastic elastomer (for example, TPU) and a thermosetting elastomer (for example, silicone) may be used.

Where the sheet members 86 and 96 are formed of a thermoplastic elastomer, a molding method such as T-die extrusion molding or injection molding is used. Where they are formed of a thermosetting elastomer, a molding method such as mold casting molding is used. After the sheet members are formed by the molding methods, they are sized to a predetermined shape, and the sized pieces are joined by adhesion, welding, or the like, to form bag-shaped structure 81 and 91. Where a thermoplastic elastomer is used, a high frequency welder or laser welding is used as a joining method. Where a thermosetting elastomer is used, a molecular adhesive agent is used.

The fluid circuit 7 is constituted by the case 11, the pump 14, the flow path portion 15, the on-off valves 16, the pressure sensors 17, the pressing cuff 71 and the sensing cuff 73. A specific example of the fluid circuit 7 will be described, with the two on-off valves 16 of the fluid circuit 7 being referred to as a first on-off valve 16A and a second on-off valve 16B, and with the two pressure sensors 17 being referred to as a first pressure sensor 17A and a second pressure sensor 17B.

As shown in FIG. 4, the fluid circuit 7 includes a first flow path 7a that connects the pump 14 to the pressing cuff 71, a second flow path 7b that branches from an intermediate portion of the first flow path 7a and that connects the pump 14 to the sensing cuff 73, and a third flow path 7c that connects the first flow path 7a to the atmosphere. The first flow path 7a includes a first pressure sensor 17A. The first on-off valve 16A is provided between the first flow path 7a and the second flow path 7b. The second flow path 7b includes a second pressure sensor 17B. The second on-off valve 16B is provided between the first flow path 7a and the third flow path 7c.

In the fluid circuit 7 mentioned above, when the first on-off valve 16A and the second on-off valve 16B are closed, only the first flow path 7a is connected to the pump 14, so that the pump 14 and the pressing cuff 71 are fluidly connected. In the fluid circuit 7, when the first on-off valve 16A is opened and the second on-off valve 16B is closed, the first flow path 7a and the second flow path 7b are connected, so that the pump 14 and the pressing cuff 71 are fluidly connected and the pump 14 and the sensing cuff 73 are fluidly connected. In the fluid circuit 7, when the first on-off valve 16A is closed and the second on-off valve 16B is opened, the first flow path 7a and the third flow path 7c are connected, so that the pressing cuff 71 and the atmosphere are fluidly connected. In the fluid circuit 7, when the first on-off valve 16A and the second on-off valve 16B are opened, the first flow path 7a, the second flow path 7b and the third flow path 7c are connected, so that the pressing cuff 71, the sensing cuff 73 and the atmosphere are fluidly connected.

Figure 16:
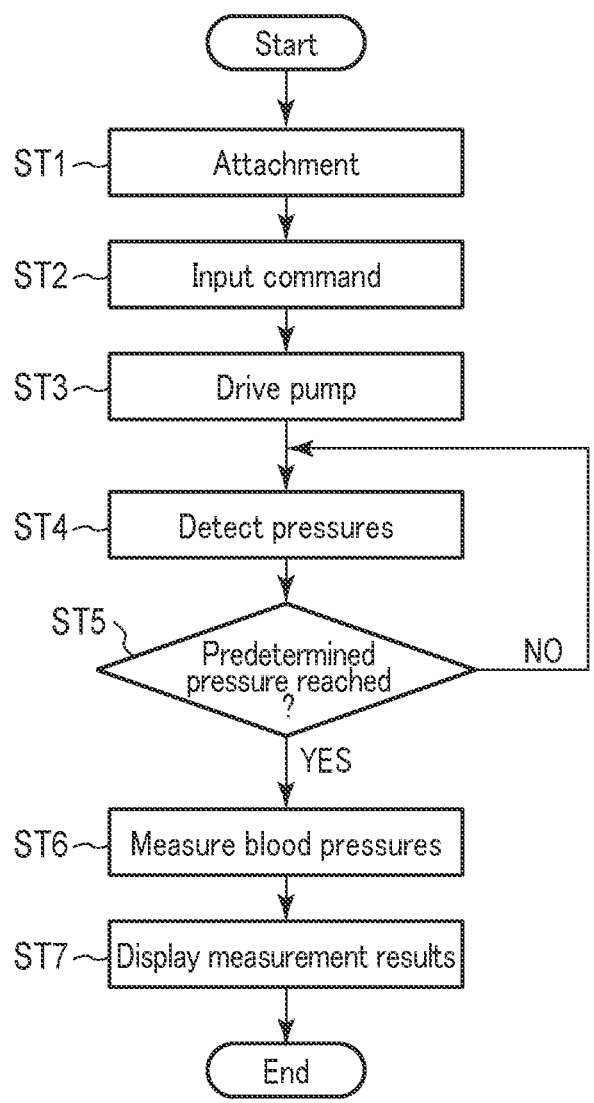
FIG. 16 is a flowchart showing an example of how the blood pressure measurement device is used.
Figure 17:
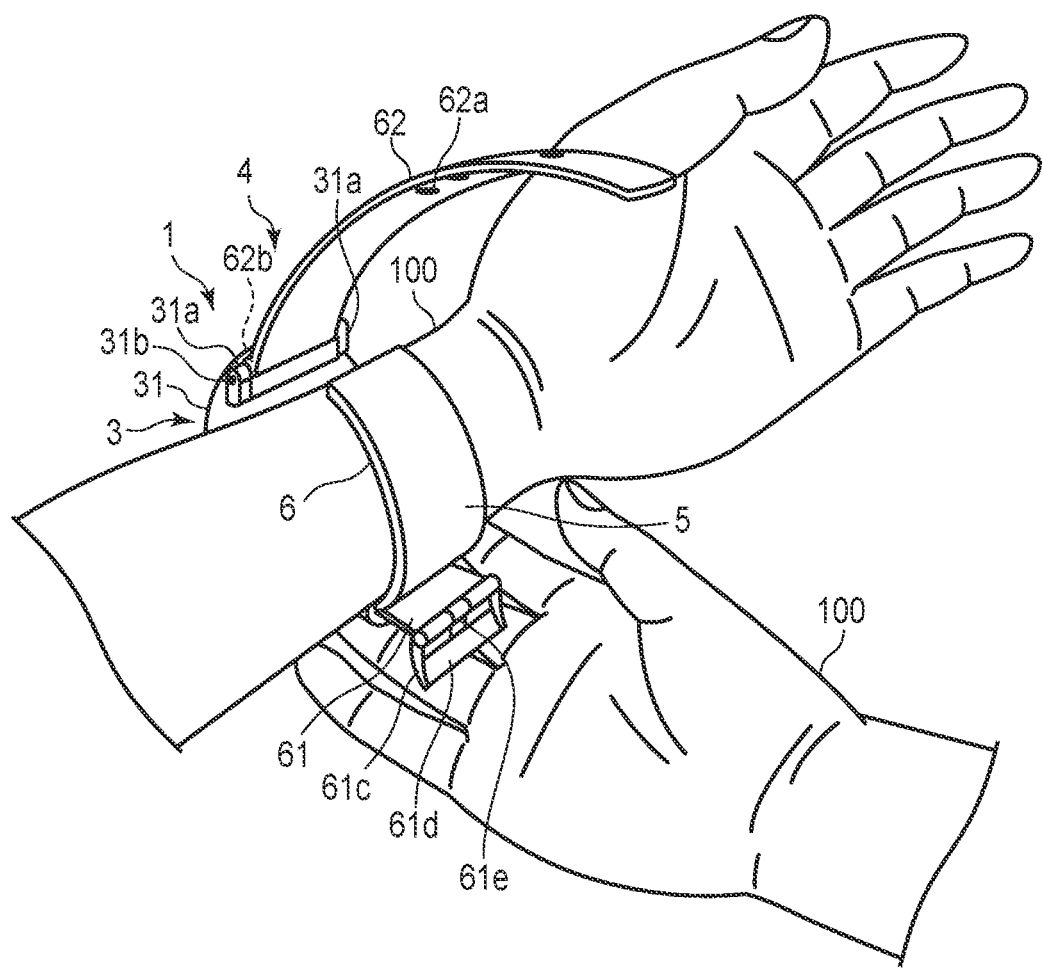
FIG. 17 is a perspective view showing an example of how the blood pressure measurement device is wrapped around the wrist.
Figure 18:
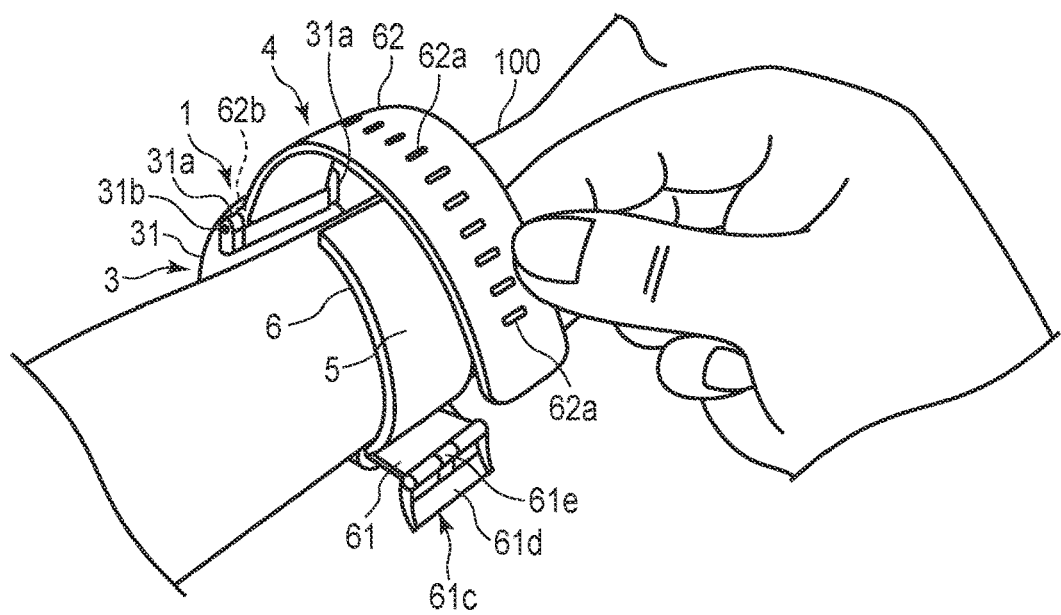
FIG. 18 is a perspective view showing an example of how the blood pressure measurement device is wrapped around the wrist.
Figure 19:
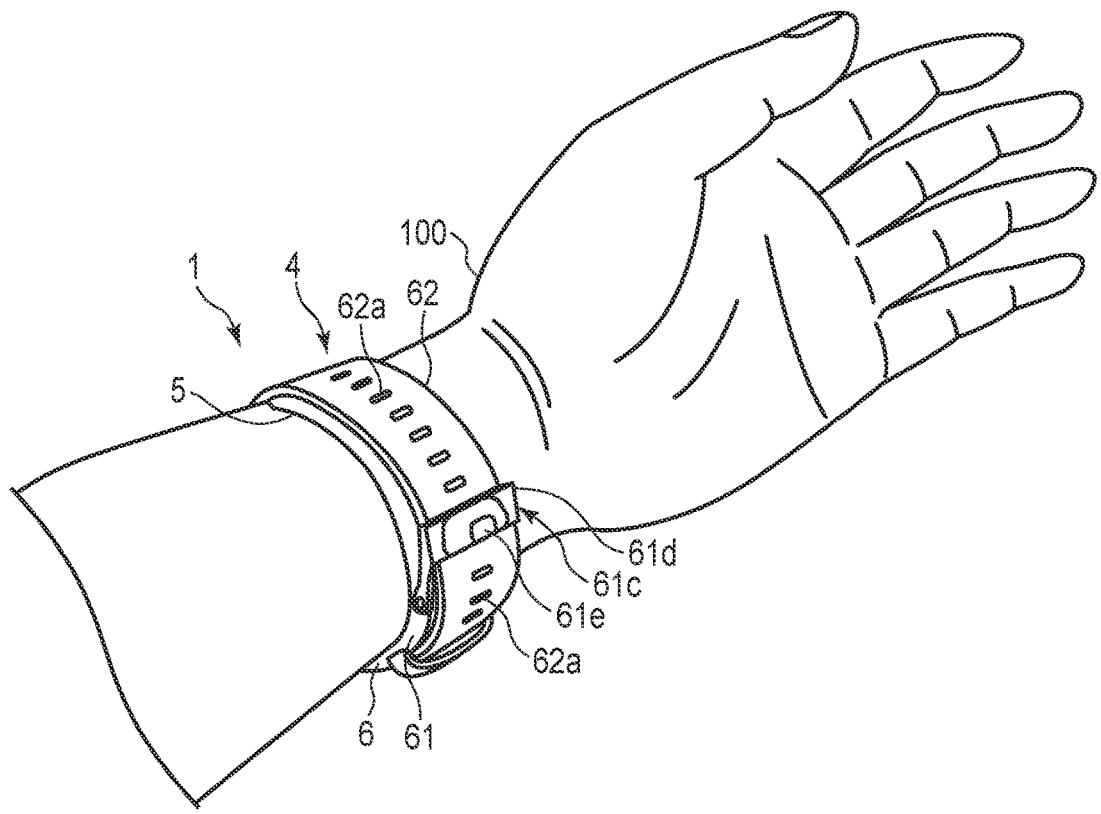
FIG. 19 is a perspective view showing an example of how the blood pressure measurement device is wrapped around the wrist.

Next, an example of how a blood pressure value is measured by the blood pressure measurement device 1 will be described with reference to FIGS. 16 to 19. FIG. 16 is a flowchart showing an example of blood pressure measurement using the blood pressure measurement device 1, and illustrates both the movement of a user and the operation of the control unit 59. FIGS. 17 to 19 show an example in which the user wears the blood pressure measurement device 1 on the wrist 100.

First, the user attaches the blood pressure measurement device 1 to the wrist 100 (step ST1). Specifically, for example, the user inserts one of the wrists 100 into the curler 5, as shown in FIG. 17.

At the time, in the blood pressure measurement device 1, the device body 3 and the sensing cuff 73 are arranged at opposing positions of the curler 5, so that the sensing cuff 73 is arranged in the region where the palm side artery 110 of the wrist 100 exists. As a result, the device body 3 is arranged on the back side of the wrist 100. Next, as shown in FIG. 18, the user passes the second strap 62 through the frame-shaped body 61d of the buckle 61c of the first strap 61, using the hand different from the hand on which the blood pressure measurement device 1 is worn. Next, the user pulls the second strap 62 to bring the member on the inner peripheral surface side of the curler 5, that is, the cuff structure 6, into close contact with the wrist 100, and inserts the stick 61e in a small hole 62a. Thus, as shown in FIG. 19, the first strap 61 and the second strap 62 are connected, and the blood pressure measurement device 1 is attached to the wrist 100.

Next, the user operates the operation unit 13 to input a command corresponding to the start of blood pressure measurement. In response to the command input operation, the operation unit 13 outputs an electric signal corresponding to the start of measurement to the control unit 59 (step ST2). Upon receipt of the electric signal, the control unit 59 opens the first on-off valve 16A, closes the second on-off valve 16B, and drives the pump 14, so that compressed air is supplied to the pressing cuff 71 and the sensing cuff 73 via the first flow path 7a and the second flow path 7b (step ST3). As a result, the pressing cuff 71 and the sensing cuff 73 start to inflate.

The first pressure sensor 17A and the second pressure sensor 17B detect the pressures of the pressing cuff 71 and the sensing cuff 73, respectively, and output electric signals corresponding to the pressures to the control unit 59 (step ST4). Based on the received electric signals, the control unit 59 determines whether or not the pressures in the internal spaces of the pressing cuff 71 and sensing cuff 73 can reach a predetermined pressure for blood pressure measurement (step ST5). For example, if the internal pressure of the pressing cuff 71 has not reached the predetermined pressure and the internal pressure of the sensing cuff 73 has reached the predetermined pressure, then the control unit 59 closes the first on-off valve 16A and supplies compressed air through the flow path 7a.

When both the internal pressure of the pressing cuff 71 and the internal pressure of the sensing cuff 73 have reached the predetermined pressure, the control unit 59 stops driving the pump 14 (YES in step ST5). At the time, as shown in FIG. 14, the pressing cuff 71 is sufficiently inflated, and the inflated pressing cuff 71 presses the wrist 100 and the back plate 72. The pressing cuff 71 may be wrinkled along the guide portion 84.

Further, the sensing cuff 73 is supplied with a predetermined amount of air so that the internal pressure becomes the pressure required for blood pressure measurement, and is thus inflated, and the back plate 72 pressed by the pressing cuff 71 presses the sensing cuff 73 against the wrist 100. Therefore, the sensing cuff 73 pushes the artery 110 in the wrist 100 and presses the artery 110 as shown in FIG. 15.

In addition, the control unit 59 controls the second on-off valve 16B to repeatedly open and close the second on-off valve 16B, or adjusts the opening of the second on-off valve 16B, such that the pressure in the internal space of the pressing cuff 71 is decreased. In the process of this pressure decrease, the control unit 59 obtains measurement results, such as blood pressure values, e.g., systolic blood pressure and diastolic blood pressure, a heart rate or the like, based on the electric signals output from the second pressure sensor 17B.

The timing at which the first on-off valve 16A and the second on-off valve 16B are opened and closed during blood pressure measurement can be determined as appropriate. Although a description was given referring to an example in which the control unit 59 calculates blood pressure in the process of increasing the pressure in the pressing cuff 71, the blood pressure may be calculated in the pressure decreasing process of the pressing cuff 71 or may be calculated in both the pressure increasing process and the pressure decreasing process of the pressing cuff 71. Next, the control unit 59 outputs image signals corresponding to the obtained measurement results to the display unit 12.

Upon receipt of the image signals, the display unit 12 displays the measurement results on the screen. The user confirms the measurement results by looking at the display unit 12. After the measurement, the user removes the stick 61e from the small hole 62a, removes the second strap 62 from the frame-shaped body 61d, and pulls the wrist 100 off the curler 5, thereby detaching the blood pressure measurement device 1 from the wrist 100.

In the blood pressure measurement device 1 according to the embodiment configured as described above, the first connected portion 38A of the flow path cover 34 to which the connecting portion 83 of the tube 82 of the pressing cuff 71 is connected has the recess 39 and the nozzle 40. The connecting portion 83 is housed in the recess 39. Furthermore, in the blood pressure measurement device 1, the second connected portion 38B of the flow path cover 34 to which the connecting portion 93 of the tube 92 of the sensing cuff 73 is connected has the recess 45 and the nozzle. 50. The connecting portion 93 is housed in the recess 45.

With this configuration, the thickness of the integrated body made up of the base, the flow path cover and the connecting portion 83 can be decreased, so that the blood pressure measurement device can be made thin.

Furthermore, a plurality of projections 43 are formed on the base 33 side end surface 41a of the recess 39. For example, even if the flow path cover 34 does not have an intended shape or if the flow path cover 34 warps, the projections 43 come into contact with the back surface of the base 33. Since the gap between the surface 41 of the recess 39 and the base 33 can be maintained, the nozzle 40 can be prevented from being blocked. Likewise, the projections 48 are formed in the recess 45, and the gap between the surface 46 of the recess 45 and the base 33 can be maintained thereby, so that the nozzle 50 can be prevented from being blocked.

Furthermore, the end surface 41a is formed with the groove 42 communicating with the nozzle 40 and extending to the peripheral surface 41b of the recess 39, so that the air from the space between the flow path cover 34 and the base 33 can be smoothly supplied to the nozzle 40, and the air from the nozzle 40 can be smoothly guided to the space between the flow path cover 34 and the base 33. Likewise, the end surface 46a is formed with the groove 47 communicating with the nozzle 50 and extending to the peripheral surface 46b, so that the air from the space between the flow path cover 34 and the base 33 can be smoothly guided to the nozzle 50, and the air from the nozzle 50 can be smoothly guided to the space between the flow path cover 34 and the base 33.

In the present embodiment, the device body 3 is arranged on the back side of the wrist 100, but the device body 3 may be arranged on the palm side of the wrist 100. That is, the device body 3 may be fixed to the outer surface of the region of the curler 5 where the sensing cuff 73 is arranged. In the blood pressure measurement device 1 having this configuration, since the device body 3 is arranged on the palm side and is thus arranged in the region where the artery of the wrist 100 exists, the distance to the sensing cuff 73 is short, and the tube 92 provided for the sensing cuff 73 can be short.

Figure 20:
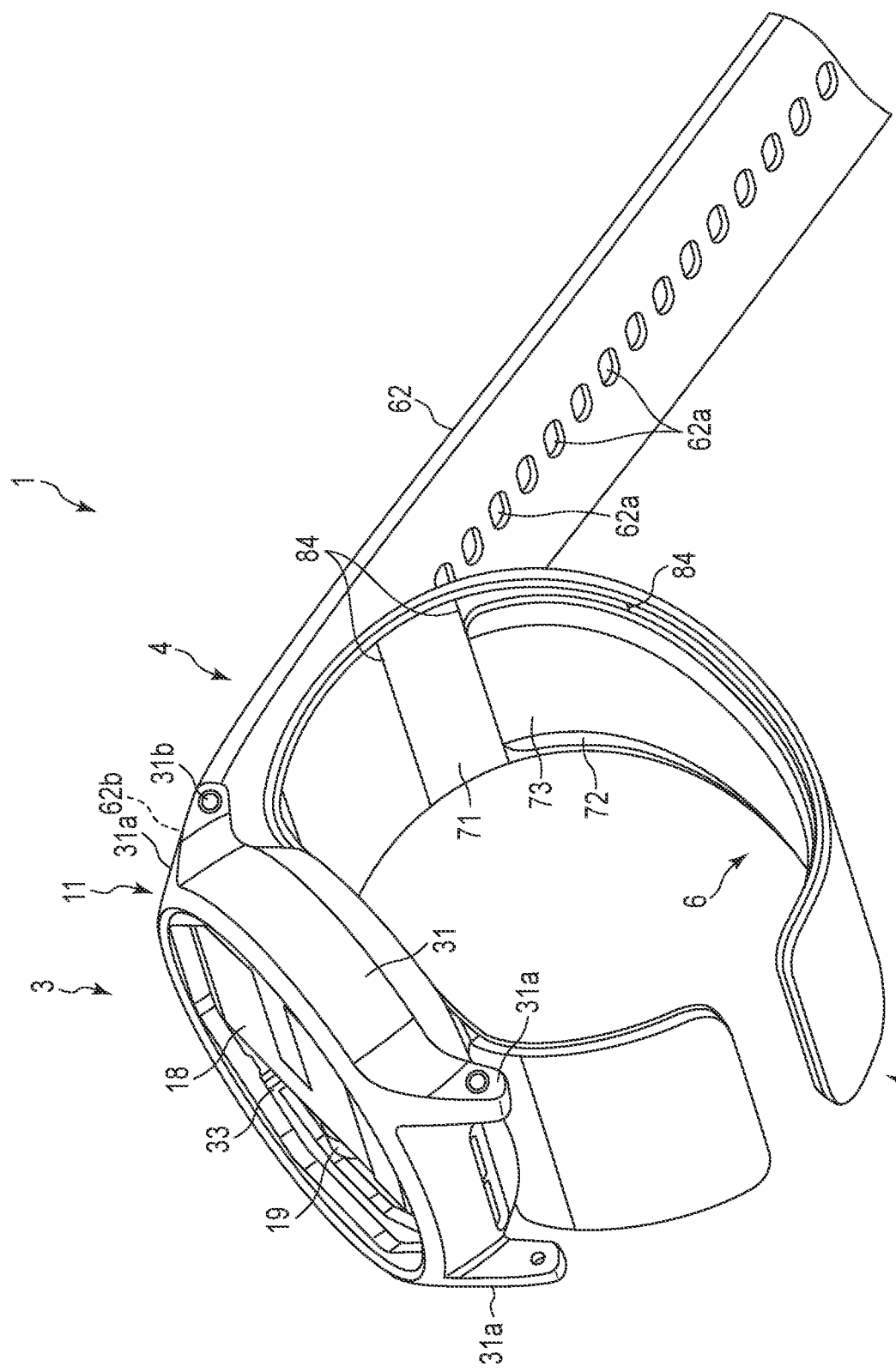
FIG. 20 is a perspective view showing another configuration of the blood pressure measurement device.

In the present embodiment, the curler 5 is configured such that one end is fixed between the base 33 and the flow path cover 34 of the device body 3 and the back cover 36, and the other end is arranged close to the device body 3. As shown in FIG. 20, however, the curler 5 may be fixed to the outer surface of the back cover 36 such that its one end is projected from one pair of lugs 31a of the back cover 36 and the other end is projected from the other pair of lugs 31a and extended to a position adjacent to the one end.

The above-described embodiment is merely an example of the present invention in all respects. Needless to say, various improvements and modifications can be made without departing from the scope of the present invention. That is, in implementing the present invention, a specific configuration according to the embodiment may be adopted as appropriate.

REFERENCE SIGNS LIST

1 . . . Blood Pressure Measurement Device
3 . . . Device Body
4 . . . Strap
5 . . . Curler
6 . . . Cuff Structure
7 . . . Fluid Circuit
7a . . . First Flow Path
7b . . . Second Flow Path
7c . . . Third Flow Path
11 . . . Case
12 . . . Display Unit
13 . . . Operation Unit
14 . . . Pump
15 . . . Flow Path Portion
16 . . . On-Off Valve
16A . . . First On-Off Valve
16B . . . Second On-Off Valve
17 . . . Pressure Sensor
17A . . . First Pressure Sensor
17B . . . Second Pressure Sensor
18 . . . Power Supply Unit
19 . . . Vibration Motor
20 . . . Control Board
31 . . . Outer Case
31a . . . Lug
31b . . . Spring Rod
32 . . . Windshield
33 . . . Base
33b . . . Surface
34 . . . Flow Path Cover
34a . . . Surface
34b . . . Rib
34b1 . . . First Rib
34b2 . . . Second Rib
34c . . . First Region
34d . . . Second Region
34e . . . Back Surface
36 . . . Back Cover
36a . . . Screw
37 . . . Flow Path Tube
38A . . . First Connected Portion
38B . . . Second Connected Portion
39 . . . Recess
40 . . . Nozzle
41 . . . Surface
41a . . . End Surface
41b . . . Peripheral Surface
42 . . . Groove
43 . . . Projection
44 . . . Back Surface
44a . . . Bottom Surface
44b . . . Peripheral Surface
45 . . . Recess
46 . . . Surface
46 . . . End Surface 46b . . . Peripheral Surface
47 . . . Groove
48 . . . Projection
49 . . . Back Surface
49a . . . Bottom Surface
49b . . . Inner Peripheral Surface
50 . . . Nozzle
51 . . . Button
52 . . . Sensor
53 . . . Touch Panel
55 . . . Board
56 . . . Acceleration Sensor
57 . . . Communication Unit
58 . . . Storage Unit
59 . . . Control Unit
61 . . . First Strap
61a . . . First Hole Portion
61b . . . Second Hole Portion
61c . . . Buckle
61d . . . Frame-Shaped Body
61e . . . Stick
62 . . . Second Strap
62a . . . Small Hole
71 . . . Pressing Cuff
72 . . . Back Plate
72a . . . Groove
73 . . . Sensing Cuff
81 . . . Bag-Shaped Structure
81 . . . Air Bag
82 . . . Tube
83 . . . Connecting Portion
86 . . . Sheet Member
86a . . . First Sheet Member
86a1 . . . Outer Surface
86b . . . Second Sheet Member
86b1 . . . Opening
86c . . . Third Sheet Member
86c1 . . . Opening
86d . . . Fourth Sheet Member
91 . . . Bag-Shaped Structure
91 . . . Air Bag
92 . . . Tube
93 . . . Connecting Portion
96 . . . Sheet Member
96a . . . Fifth Sheet Member
96b . . . Sixth Sheet Member
100 . . . Wrist
110 . . . Artery

The invention claimed is:

1. A blood pressure measurement device comprising:
a base;
a flow path cover that is fixed to the base and defines a flow path portion with reference to the base;
a rib that is on a base side of the flow path cover and that is fixed to the base, the rib forming the flow path portion;
a recess that is arranged in an area surrounded by the rib of the flow path cover and that includes (i) a first outer surface, which is on the base side of the flow path cover and part of which is projected toward the base, and (ii) a second outer surface, which is on a side of the flow path cover opposite to the base side and part of which is depressed toward the base, the recess formed in the flow path cover such that the recess projects on a side of the base, and projections abut the base and are provided to maintain a gap between the first outer surface and the base;
a nozzle that is formed on the second outer surface of the recess and communicates with the flow path portion;
a cuff that is connected to the nozzle and that is inflated when a fluid is supplied to an internal space; and
a pump that supplies the fluid to the internal space of the cuff;
wherein the base holds the pump.

2. The blood pressure measurement device according to claim 1,
wherein the projections are formed on the first outer surface of the recess on the base side and are located at a position away from a hole of the nozzle.

3. The blood pressure measurement device according to claim 1, further comprising:
a groove formed in an end surface of the recess on the base side and extending from a hole of the nozzle to an outer peripheral surface of the recess.

* * * * *